US012633413B1

(12) United States Patent
Alzaydi

(10) Patent No.: US 12,633,413 B1
(45) Date of Patent: May 19, 2026

(54) SYSTEM AND METHOD FOR GENERATING MULTIMODAL DIAGNOSTIC OUTPUT RELATED TO PATHOLOGICAL CONDITION OF A PATIENT

(71) Applicant: KING FAHD UNIVERSITY OF PETROLEUM AND MINERALS, Dhahran (SA)

(72) Inventor: Ammar Ayad Alzaydi, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 19/363,310

(22) Filed: Oct. 20, 2025

(51) Int. Cl.
*A61B 5/00* (2006.01)
*A61B 6/00* (2006.01)
(Continued)

(52) U.S. Cl.
CPC .......... *G16H 50/20* (2018.01); *A61B 6/5205* (2013.01); *G06F 40/284* (2020.01); *G06T 3/40* (2013.01);
(Continued)

(58) Field of Classification Search
CPC ...... G16H 50/20; G16H 50/30; G06F 40/284; G06V 10/40; G06V 10/82; G06V 10/72;
(Continued)

(56) References Cited

U.S. PATENT DOCUMENTS

2021/0378514 A1* 12/2021 Moenning .............. G16H 50/30
2022/0383346 A1* 12/2022 Barreto .............. G06Q 30/0245
(Continued)

FOREIGN PATENT DOCUMENTS

IN    2025/21053161 A    6/2025

OTHER PUBLICATIONS

K. Aditya Shastry, et al., "An integrated deep learning and natural language processing approach for continuous remote monitoring in digital health"; Decision Analytics Journal, vol. 8. Sep. 2023, 14 pages.

(Continued)

*Primary Examiner* — Michael J Vanchy, Jr.
(74) *Attorney, Agent, or Firm* — Oblon, McClelland, Maier & Neustadt, L.L.P.

(57) ABSTRACT

A method and a system for generating a multimodal diagnostic output related to a pathological condition of a patient includes at least one processor and a memory storing instructions executable by the processor to receive medical image data and narrative data of the patient. The medical image data is preprocessed through normalization, while the narrative data is standardized to ensure consistency. The preprocessed image data is input into a trained deep residual network (ResNet) to extract quantitative imaging features indicative of the pathological condition. In parallel, the preprocessed narrative data is input into a thematic analysis module to derive thematic codes reflecting emotional, cognitive, or social factors of the patient. The extracted imaging features and thematic codes are fused into a combined feature vector, which is processed by an integrated diagnostic model to generate a multimodal diagnostic output that enhances clinical precision and contextual interpretation.

20 Claims, 21 Drawing Sheets

(51) Int. Cl.

| | |
|---|---|
| *G06F 40/284* | (2020.01) |
| *G06T 3/40* | (2006.01) |
| *G06T 3/60* | (2006.01) |
| *G06T 7/00* | (2017.01) |
| *G06V 10/40* | (2022.01) |
| *G06V 10/72* | (2022.01) |
| *G06V 10/764* | (2022.01) |
| *G06V 10/774* | (2022.01) |
| *G06V 10/776* | (2022.01) |
| *G06V 10/82* | (2022.01) |
| *G16H 50/20* | (2018.01) |
| *G16H 50/30* | (2018.01) |
| *A61B 6/50* | (2024.01) |

(52) U.S. Cl.
CPC .............. *G06T 3/60* (2013.01); *G06T 7/0012* (2013.01); *G06V 10/40* (2022.01); *G06V 10/72* (2022.01); *G06V 10/764* (2022.01); *G06V 10/774* (2022.01); *G06V 10/776* (2022.01); *G06V 10/82* (2022.01); *G16H 50/30* (2018.01); *A61B 6/501* (2013.01); *A61B 6/502* (2013.01); *G06T 2207/10081* (2013.01); *G06T 2207/20081* (2013.01); *G06T 2207/20084* (2013.01); *G06V 2201/03* (2022.01)

(58) Field of Classification Search
CPC .. G06V 10/774; G06V 10/776; G06V 10/764; G06V 2201/03; A61B 6/5205; A61B 6/501; A61B 6/502; G06T 3/40; G06T 3/60; G06T 7/0012; G06T 2207/10081; G06T 2207/20081; G06T 2207/20084
See application file for complete search history.

(56) References Cited

U.S. PATENT DOCUMENTS

2024/0221950 A1* 7/2024 Kollada ............... A61B 5/0205
2025/0046447 A1 2/2025 Babu et al.

OTHER PUBLICATIONS

Ammar Alzaydi. "Integrating Deep Residual Learning and Thematic Analysis in a Hybrid Framework for Precision Oncology: Advancing Cancer Diagnosis and Personalized Treatment", International Journal of Engineering and Management Research, vol. 15, No. 2. Apr. 2025: 16 Pages.

* cited by examiner

1302

1304

1400

1500

SYSTEM AND METHOD FOR GENERATING MULTIMODAL DIAGNOSTIC OUTPUT RELATED TO PATHOLOGICAL CONDITION OF A PATIENT

STATEMENT OF PRIOR DISCLOSURE BY AN INVENTOR

Aspects of the present disclosure are described in A. A. Alzaydi., "Integrating Deep Residual Learning and Thematic Analysis in a Hybrid Framework for Precision Oncology: Advancing Cancer Diagnosis and Personalized Treatment," *International Journal of Engineering and Management Research*, Vol. 15 No. 2 (2025) which is incorporated herein by reference in its entirety.

BACKGROUND

Technical Field

The present disclosure is directed to a method and a system for generating a multimodal diagnostic output related to a pathological condition of a patient.

Description of Related Art

The background description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Cancer continues to be a major cause of morbidity and mortality worldwide and remains the subject of extensive diagnostic and therapeutic research. Conventional diagnostic practice relies primarily upon medical imaging (for example, radiology modalities such as CT and MRI) and histopathological examination, together with laboratory biomarkers and clinician interpretation. While these modalities provide essential biological and morphological information, they possess well-known limitations, including inter- and intra-observer variability in visual interpretation, modality-specific risks (for example, cumulative ionizing radiation from CT imaging), and incomplete sensitivity or specificity across diverse patient sub-populations (for example, reduced sensitivity of certain blood-based biomarkers in particular demographic groups). These limitations motivate continued development of diagnostic tools that improve detection, reduce diagnostic uncertainty, and generalize across heterogeneous patient cohorts.

Over the last decade, artificial intelligence and, in particular, deep learning techniques have been widely applied to medical-image analysis. Convolutional neural networks (CNNs) and deep residual networks (ResNets) enable training of very deep architectures by introducing residual connections that mitigate vanishing-gradient effects. Residual-based architectures (for example, ResNet-50 and derivative models) and attention-augmented residual networks have been used in numerous oncology-related imaging tasks, including histopathological classification, cancer lesion detection in radiology, image denoising for X-ray/CT, and certain prognostic estimations. Modified residual attention networks and other residual-derived topologies have been reported to achieve high performance on specific binary and multiclass histopathology classification tasks, and residual-learning-based denoisers have been shown to improve image quality in noisy medical imaging domains. Such prior work demonstrates the technical utility of deep residual learning for extracting hierarchical visual features that are useful for automated diagnostic prediction when trained on sufficiently rich and representative image datasets.

Notwithstanding these advances, several technical and practical challenges remain with respect to applying deep learning to clinical diagnostics. First, deep models generally require large volumes of labeled, phenotypically diverse training data to generalize reliably; publicly-available and institutional datasets often underrepresent minority populations and rare phenotypes, which may limit external validity. Second, distributional shifts in deployment environments (for example, differing scanner hardware, staining protocols, image acquisition parameters, or clinical workflows) may degrade model performance relative to curated benchmark settings. Third, deep learning models frequently exhibit limited transparency or explainability, giving rise to so-called "black box" concerns that hinder clinician trust, clinical governance and regulatory clearance. Fourth, state-of-the-art image-centric systems typically operate on structured imaging inputs and do not account for psychosocial, cognitive, or narrative information that influences clinical decision-making, patient adherence and outcomes.

In parallel, qualitative research methodologies have been developed and widely applied to capture patient-centered experiences. Thematic analysis (TA), for example, the six-phase approach of Braun & Clarke, is a robust qualitative method for identifying, coding and characterizing recurrent themes in narrative data such as patient interviews, clinical notes and survey responses. TA has been applied in oncology-related research to surface domains including emotional responses (for example, fear, sadness, anger), cognitive processing (for example, insight formation, causality attribution), and social dynamics (for example, support systems, preferences for shared decision-making). These thematic findings have demonstrable relevance to clinical communication, psychosocial support strategies, and overall patient outcomes; however, such qualitative outputs are typically not encoded into machine-usable representations that are integrated with automated imaging diagnostics.

Prior multimodal biomedical AI efforts have focused predominantly on combining structured modalities (for example, imaging plus genomics or structured clinical variables) and have demonstrated that fusing heterogeneous numerical information can improve prognostic and diagnostic performance. By contrast, the programmatic conversion of unstructured narrative data, processed through rigorous qualitative methods such as Thematic Analysis, into quantified thematic vectors that are suitable for algorithmic fusion with deep image features has been only sparsely explored in the literature and remains largely absent from commercial diagnostic offerings. Prior systems provide a clinically-oriented, repeatable pipeline that: (i) performs inductive thematic coding of patient narratives using a reproducible TA workflow; (ii) transforms coded themes into numeric vectors or scores; and (iii) systematically fuses those thematic representations with deep residual image feature vectors within a decision-support or meta-classification architecture.

Additional technical considerations relevant to any multimodal diagnostic system include secure data linkage, patient privacy, analytic reliability, and end-user interpretability. In an embodiment, image and narrative inputs are de-identified and linked using irreversible identifiers (for example, hashed identifiers) and transported and stored via encrypted channels, thereby enabling multimodal fusion while protecting protected health information.

In an embodiment, when synthetic datasets are used for pre-clinical validation, the generation process is documented and evaluated. For example, synthetic histopathology images may be produced using generative adversarial networks (GANs) and synthetic narratives may be produced using controlled natural-language generation (NLG) models; the realism and diversity of such synthetic outputs are assessed prior to use by objective measures (for example, Fréchet Inception Distance) and by expert clinician review to confirm that clinically relevant variation is represented.

In an embodiment, the qualitative analysis pipeline enforces coder reliability and adjudication procedures before thematic outputs are admitted to model training. For example, multiple coders independently code a sample set, inter-coder agreement is computed (for example, Cohen's kappa), and discrepant codes are resolved through a documented reconciliation workflow. Themes are converted to numeric vectors only after passing these reliability checks.

In an embodiment, the system produces interpretable outputs at both the image and narrative levels. Image-level interpretability may include saliency maps, segmented regions of interest, or ranked visual features linked to the diagnostic decision. Narrative-level interpretability may include named themes, normalized theme-scores, and concise natural-language explanations that indicate how thematic signals informed the decision. The system is further configured to operate in fallback modes when one modality is unavailable: for example, operating in image-only mode when narrative data are missing, and in narrative-only mode when imaging is unavailable, while preserving auditability of the decision process.

Regulatory, interoperability, and deployment constraints are also material to system design. In an embodiment, the software is developed with audit logging and performance documentation appropriate for Software as a Medical Device (SaMD) submissions. The system supports common healthcare data standards (for example, DICOM/PACS for imaging and FHIR/HL7 for clinical data exchange) and implements privacy and security controls (for example, role-based access, TLS encryption, and data governance consistent with HIPAA or equivalent laws).

Finally, socio-technical factors must be addressed for safe and effective deployment. In an embodiment, the design contemplates clinician workflow integration, mechanisms to monitor and mitigate bias in narrative signals, and plans for prospective validation across demographically diverse cohorts under institutional review board (IRB) oversight.

Accordingly, there exists a need for a modular, clinically-viable diagnostic framework that (i) enables secure multimodal linkage of imaging and narrative data, (ii) provides documented and validated synthetic data workflows when used, (iii) enforces reliability controls on thematic coding, (iv) furnishes interpretable, auditable outputs with robust fallback behavior, and (v) is implementable within regulated, interoperable clinical environments.

Accordingly, there remains a need for improved DC-DC converter topologies that overcome the limitations of the prior art.

SUMMARY

In an exemplary embodiment, a method for generating a multimodal diagnostic output related to a pathological condition of a patient is disclosed. The method includes receiving, by at least one processor, medical image data and narrative data of the patient. The method includes preprocessing, by the at least one processor, the medical image data and the narrative data by normalizing the medical image data and standardizing the narrative data. The method includes providing the preprocessed medical image data as inputs to a trained deep residual network (ResNet) to extract one or more quantitative imaging features indicative of the pathological condition. The method includes providing the preprocessed narrative data as inputs to a thematic analysis module for extracting one or more thematic codes representing emotional, cognitive or social factors of the patient from the narrative data. The method includes fusing vector representations of the one or more quantitative imaging features and the one or more thematic codes into a combined feature vector. The method includes providing the combined feature vector as inputs an integrated diagnostic model configured to generate the multimodal diagnostic output related to the pathological condition of the patient.

In an exemplary embodiment, a system for generating a multimodal diagnostic output related to a pathological condition of a patient is disclosed. The system includes at least one processor and a memory storing instructions that, when executed by the at least one processor, cause the at least one processor to receive medical image data and narrative data of the patient. The at least one processor is configured to preprocess the medical image data and the narrative data by normalization of the medical image data and standardization of the narrative data. The at least one processor is configured to input the preprocessed medical image data into a trained deep residual network (ResNet) to extract one or more quantitative imaging features indicative of the pathological condition. The at least one processor is configured to input the preprocessed narrative data into a thematic analysis module to extract one or more thematic codes representing emotional, cognitive or social factors of the patient from the narrative data. The at least one processor is configured to fuse vector representations of the one or more quantitative imaging features and the one or more thematic codes into a combined feature vector. The at least one processor is configured to input the combined feature vector into an integrated diagnostic model configured to generate the multimodal diagnostic output related to the pathological condition of the patient.

In another exemplary embodiment, the foregoing general description of the illustrative embodiments and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1:
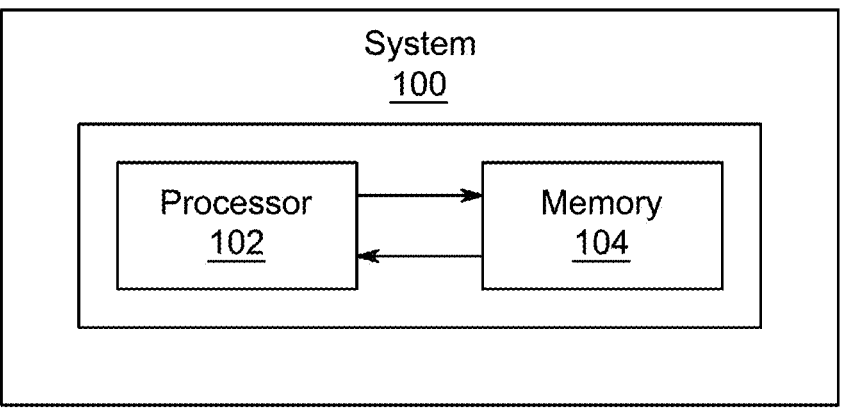
FIG. 1 shows a block diagram of a system for generating a multimodal diagnostic output related to a pathological condition of a patient, according to an embodiment of the present invention.

In the drawings, like reference numerals designate identical or corresponding parts throughout the several views. Further, as used herein, the words "a", "an" and the like generally carry a meaning of "one or more", unless stated otherwise.

Furthermore, the terms "approximately," "approximate", "about" and similar terms generally refer to ranges that include the identified value within a margin of 20%, 10%, or preferably 5%, and any values therebetween.

The present disclosure provides a multimodal diagnostic system and method that integrates deep residual learning with thematic analysis to produce context-enriched cancer diagnostics and personalized treatment recommendations. The system and method combine automated, high-fidelity image feature extraction from histopathological or radiological images with a repeatable thematic coding pipeline that converts patient narratives into numeric thematic representations and programmatically fuses these representations in a decision-support architecture to yield a final diagnostic label, confidence metrics, and narrative-derived interpretability cues.

In various aspects of the disclosure, non-limiting definitions of one or more terms that will be used in the document are provided below.

A term "Deep residual learning (DRL)" refers to a deep neural network training paradigm that employs residual connections (skip connections) to enable effective training of very deep convolutional architectures, such as ResNet variants, for hierarchical visual feature extraction.

A term "ResNet-50" refers to a fifty-layer residual convolutional neural network architecture that includes identity and convolutional residual blocks and that is suitable for transfer learning in medical image classification tasks.

A term "Thematic analysis (TA)" refers to a systematic qualitative analytic method (for example, the six-phase Braun & Clarke workflow) for identifying, coding and developing themes from narrative textual data, including patient interviews, clinical notes, and questionnaire responses.

A term "theme vector" refers to a numeric representation of one or more themes derived from TA, wherein each vector encodes the presence, intensity or normalized score of thematic dimensions such as emotional, cognitive or social attributes.

A term "multimodal fusion layer" refers to a computational stage that aligns, combines and processes image-derived feature vectors and theme vectors to generate a fused representation for downstream classification or decision-making (for example, via concatenation, attention-weighting, gating, or meta-classification).

Synthetic training data refers to non-identifiable, algorithmically generated datasets produced for pre-clinical model training and validation, such as synthetic histopathology images generated by generative adversarial networks (GANs) and synthetic narratives generated by controlled natural language generation (NLG) models.

The present disclosure addresses several technical challenges in AI-enabled oncology diagnostics. A first challenge is the limited contextual awareness of image-only diagnostic models, which lack structured information about a patient's psychosocial state. A second challenge is the difficulty of converting unstructured narrative data into repeatable, auditable machine-usable representations suitable for fusion with high-dimensional image features. Another challenge is ensuring that multimodal fusion preserves modality-specific interpretability, avoids undue bias from narrative signals, and remains operable when one modality is missing.

The methods and systems of the present disclosure overcome the above mentioned challenges by providing a modular architecture comprising: (i) a DRL engine (for example, a ResNet-50 based image-processing pipeline) that extracts compact, high-value visual feature vectors from pre-processed images; (ii) a TA engine that implements an inductive coding workflow, enforces inter-coder reliability, and converts coded themes into normalized theme vectors; (iii) a multimodal fusion layer that aligns patient-specific image and narrative vectors and applies adaptive weighting or gating informed by theme signals; and (iv) a decision-support module (for example, a meta-classifier or ensemble) that issues diagnostic labels, confidence scores and interpretable narrative cues. In an embodiment, the system further comprises a synthetic-data generator for controlled pre-clinical validation, a feedback unit to incorporate treatment-response labels for continuous learning, and secure linkage mechanisms for privacy-preserving multimodal alignment.

One objective of the present disclosure is to improve diagnostic accuracy, sensitivity, and specificity relative to image-only models by leveraging complementary information embedded in patient narratives. Another objective is to provide auditable, clinician-friendly interpretability at both the image and narrative levels so that model outputs can be meaningfully reviewed and acted upon. A further objective is to permit robust operation in real-world clinical environments by (i) supporting fallback modes when narrative data or images are unavailable, (ii) documenting synthetic-data realism assessments and inter-coder reliability thresholds prior to model deployment, and (iii) conforming to healthcare interoperability and privacy requirements (for example, Digital Imaging and Communications in Medicine/Picture Archiving and Communication System (DICOM/PACS), Fast Healthcare Interoperability Resources/Health Level 7 (FHIR/HL7), and appropriate encryption and consent procedures).

Accordingly, the present disclosure provides a practical, modular, and scalable solution for context-aware cancer diagnostics that unites quantitative image analysis with qualitative patient experience, enabling enhanced diagnostic performance and more personalized, patient-centered treatment planning.

FIG. 1 shows a block diagram of a system 100 for generating a multimodal diagnostic output related to a pathological condition of a patient.

In an embodiment, the system 100 comprises at least one processor 102 and a memory 104 storing executable instructions that, when executed by the at least one processor 102, implement a multimodal diagnostic pipeline for generating the multimodal diagnostic output related to the pathological condition of the patient. In an embodiment, the at least one processor 102 is a general-purpose central processing unit or a combination of a central processing unit and one or more hardware accelerators, such as graphics processing units or neural processing units. In an embodiment, the memory 104 comprises volatile memory for runtime data and non-volatile storage for model weights, datasets, configuration parameters and audit logs.

In an embodiment, the system 100 is configured to receive medical image data and narrative data of the patient through a data acquisition interface. In an embodiment, the medical image data comprises one or more image files in DICOM format or in common image formats such as TIFF, JPEG, or PNG. In an embodiment, the medical image data includes whole slide histopathology images, radiological series such as CT or MRI, or image tiles derived from whole slide images. In an embodiment, the narrative data comprises text-based inputs obtained from patient interviews, clinician notes, survey responses or transcribed audio. In an embodiment, the acquisition interface accepts input via a PACS connector, a FHIR compliant API, a secure file upload portal or EHR integration. In an embodiment, the system 100 associates each incoming data item with a de-identified patient identifier and records the association in a secure linkage table in the memory 104.

In an embodiment, the processor 102 implements a pre-processing subsystem that normalizes and standardizes incoming data prior to downstream processing. The medical image preprocessing includes resizing images to fixed tensor dimensions such as 224 by 224 pixels or 512 by 512 pixels, depending on network input requirements. The medical image preprocessing further includes colour or stain normalization for pathology images and intensity scaling to a common range, such as min to max normalization to a zero to one range, or z-score normalization. The medical image preprocessing applies data augmentation during training, including rotation, scaling, mirroring, and elastic deformation to increase generalization. The narrative preprocessing standardizes text by tokenization at word or subword level, removal of stop words when appropriate, lemmatization or stemming, normalization of punctuation, and optional de-identification by replacing protected health information tokens with placeholders. The preprocessing steps are implemented as modular pipeline stages executed by the processor 102 and parameterized by configuration files stored in the memory 104.

In an embodiment, the at least one processor 102 is configured to preprocess the medical image data by image resizing and image augmentation that includes at least one of rotation, scaling or flipping, and to standardize the narrative data by tokenizing of the narrative data, removing stop-words and lemmatizing of the narrative data. Image resizing is performed to produce fixed-dimension tensors suitable for ResNet input. Image augmentation operations are applied during training to increase robustness and include rotation, scaling and flipping as configurable operations. Narrative standardization is performed by tokenization to split text into lexical units, by removal of configured stop-words, and by lemmatizing tokens to map words to canonical forms prior to thematic coding.

In an embodiment, the processor 102 executes a ResNet-based imaging module to extract quantitative imaging features indicative of the pathological condition. In an embodiment, the ResNet based imaging module is a ResNet architecture including an input convolutional layer followed by a sequence of residual blocks. Each residual block applies convolution, batch normalization, and a non-linear activation function. In an embodiment, identity or projection skip connections provide residual learning. The output of the final convolutional block is passed through an adaptive average pooling layer and through one or more fully connected layers to produce a fixed-length image feature vector. In an embodiment, the image feature vector is a multidimensional numeric vector such as a 512-dimensional or 2048-dimensional vector. The ResNet weights persisted in the memory 104 and loaded into hardware accelerator memory by the processor 102 during inference to provide low-latency feature extraction.

In an embodiment, the trained deep residual network comprises a ResNet-50 architecture including a plurality of residual connections configured to learn one or more residual functions by applying a sequence of operations including convolution, batch normalization, and activation. The ResNet-50 receives the preprocessed medical image data and propagates tensors through convolutional layers and residual blocks. The ResNet-50 produces one or more quantitative imaging features as fixed length numeric image feature vectors that are available for fusion In an embodiment, the processor 102 executes a thematic analysis module to extract thematic codes from narrative data. In an embodiment, the thematic analysis module comprises a textual segmentation subroutine that splits narrative data into segments, such as sentences or paragraphs and associates each segment with metadata including timestamps or question identifiers. The thematic analysis module comprises an automated coding engine that assigns preliminary thematic codes to segments using a hybrid approach that combines rule-based pattern matching with supervised or unsupervised machine learning. The automated coding engine implements models such as transformer encoders, recurrent neural networks or classical classifiers to produce code assignments. The thematic analysis module further includes a coder adjudication interface that allows human coders to review and reconcile codes when automated confidence falls below a configured threshold. The thematic analysis module groups codes into higher-level factors such as emotional, cognitive and social factors based upon a mapping schema. The grouping produces numeric theme scores per factor through frequency counts, weighted presence or embedding-based similarity aggregation. In an embodiment, the produced theme vectors are stored in the memory 104.

In an embodiment, the thematic analysis module is configured to perform the thematic coding using the at least one processor 102, wherein the at least one processor 102 is configured to label one or more narrative segments of the narrative data with the one or more thematic codes, group the one or more thematic codes into one or more emotional, cognitive or social factors of the patient, generate one or more structured outputs that quantify the one or more emotional, cognitive or social factors, and vectorize the one or more structured outputs for the fusion. The processor 102 segments text into sentences or paragraph level segments and assigns thematic codes to each segment using rule based patterns, supervised classifiers, or human-in-the-loop adjudication. The processor 102 aggregates codes into named factors such as emotional, cognitive and social factors and computes numeric scores for each factor. The processor 102 converts the numeric structured outputs into fixed length theme vectors for subsequent fusion.

In an embodiment, the at least one processor 102 is configured to perform the fusion of the one or more quantitative imaging features and the one or more thematic codes, wherein the at least one processor 102 is configured to concatenate the vector representations of the one or more quantitative imaging features and the one or more thematic codes in a feature fusion layer, apply adaptive weighting of the one or more quantitative imaging features and the one or more thematic codes, align the one or more quantitative imaging features and the one or more thematic codes using a common patient identifier, and fuse the respective vector representations of the one or more quantitative imaging features and the one or more thematic codes through a shared neural layer. The processor 102 consults the patient identifier mapping table stored in the memory 104 to match image vectors and theme vectors for the same patient and clinical timepoint. The processor 102 implements adaptive weighting by computing learned gates or scalar weights based on theme vector inputs and applies those weights to image feature dimensions prior to concatenation. The processor 102 projects concatenated vectors through one or more shared neural layers to yield the combined feature vector.

In an embodiment, the processor 102 executes a vectorization stage that converts quantitative imaging features and thematic outputs into compatible vector representations for fusion. The image feature vectors are L2 normalized or standardized to a common scale. The theme vectors are normalized using min to max scaling or z-score normalization. The theme vectors may be one hot encodings for presence and absence, continuous scores for theme intensity, or dense embeddings derived from a pretrained sentence encoder fine-tuned on clinical narratives. The system 100 supports multiple vector encodings to accommodate different thematic analysis outputs.

In an embodiment, the medical image data comprises a plurality of histopathological images and a plurality of radiological images related to the pathological condition including cancer. The plurality of histopathological images may include whole slide images or extracted tiles derived from whole slide images. The plurality of radiological images may include DICOM series from modalities such as computed tomography or magnetic resonance imaging. The processor 102 executes modality specific preprocessing pipelines for each image modality and stores modality metadata in the memory 104 to permit modality aware handling and fusion.

In an embodiment, the at least one processor 102 is configured to utilize a generic image dataset to pre-train the deep residual network and to utilize medical imaging data to fine-tune the pre-trained deep residual network to extract the one or more quantitative imaging features. Pre-training on a generic image dataset initializes convolutional filters and enables transfer learning. Fine-tuning on domain specific medical imaging data updates later layers to capture histopathological and radiological textures.

In an embodiment, the narrative data comprises a text-based qualitative input obtained from the patient through patient interviews, surveys or other textual information related to patient experiences and perceptions. The narrative data may be acquired as clinician notes, questionnaire responses, or transcribed speech. The processor 102 maps each text-based qualitative input to a de identified patient identifier in the memory 104 to enable correct multimodal alignment.

In an embodiment, the at least one processor 102 is configured to receive a clinical diagnostic outcome of the patient and update at least one of the trained deep residual network or the thematic analysis module based on the clinical diagnostic outcome. The processor 102 receives validated outcomes such as pathology confirmed diagnoses or follow up clinical codes via a secure interface. The processor 102 validates incoming labels and triggers retraining, recalibration, or adjustment of model thresholds for the ResNet-50 or for the thematic analysis classifiers. The processor 102 logs model updates and performance metrics to the memory 104 for regulatory traceability.

In an embodiment, the at least one processor 102 is further configured to train and validate the integrated diagnostic model in a simulation environment, wherein the at least one processor 102 is configured to generate a plurality of synthetic histopathological images using a generative adversarial network trained on a plurality of domain-specific medical images, and to generate synthetic narrative data using a natural language generation model trained on domain-specific patient narratives, and to evaluate performance of the integrated diagnostic model, comprising a meta-classifier or an ensemble program configured to process the combined feature vector, using at least one performance metric selected from accuracy, precision, recall, F1 score, thematic coherence and thematic relevance. The processor 102 trains a GAN to produce synthetic histopathological image tiles that emulate domain specific variation. The processor 102 trains an NLG model to produce synthetic narrative examples that reflect domain specific language and themes. The processor 102 evaluates the integrated diagnostic model on combined real and synthetic hold-out sets using the recited metrics and stores evaluation artifacts in the memory 104.

Figure 2:
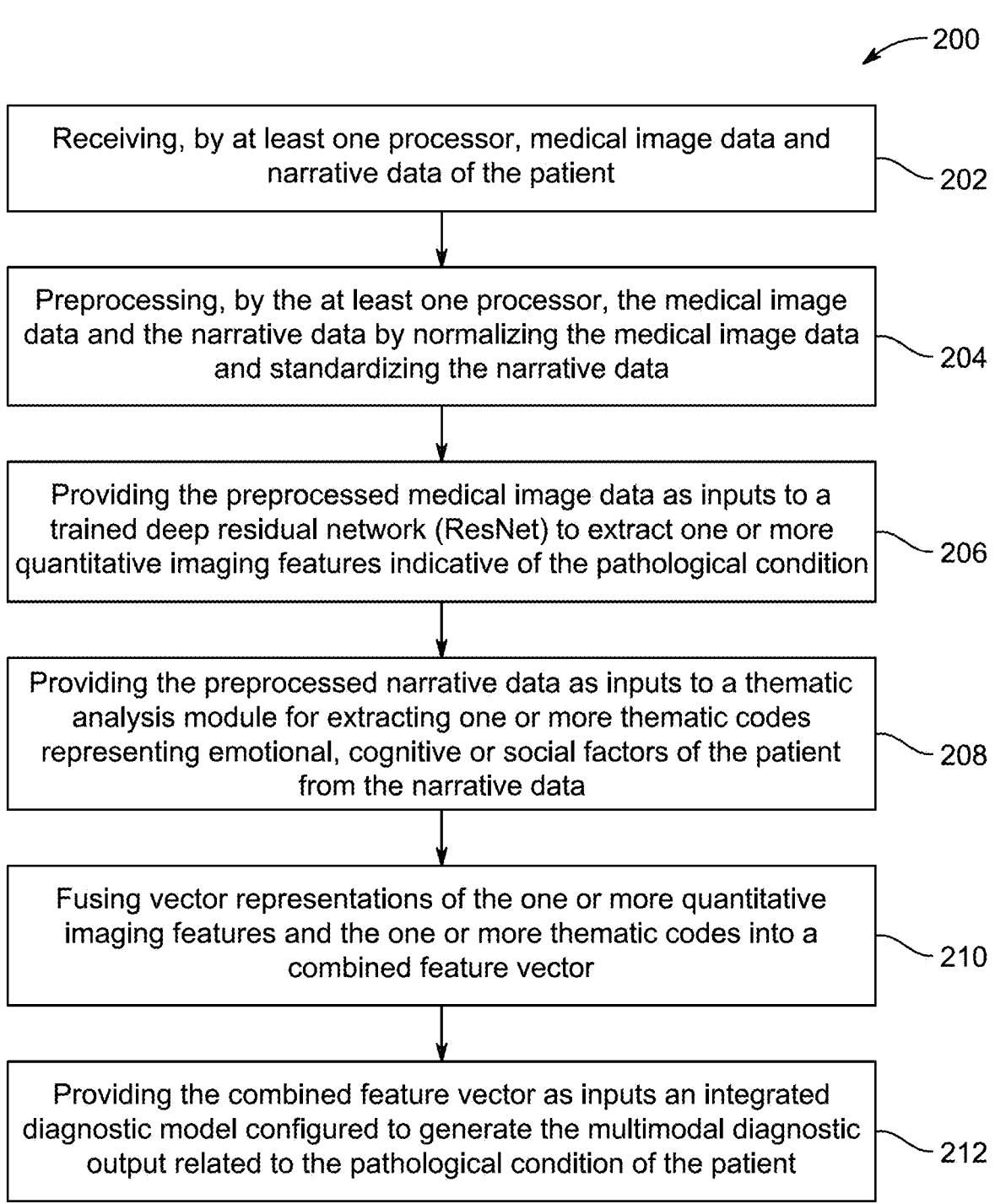
FIG. 2 shows a flow diagram of a method for generating the multimodal diagnostic output related to the pathological condition of the patient, according to an embodiment of the present invention.

FIG. 2 shows a flow diagram of a method 200 for generating the multimodal diagnostic output related to the pathological condition of the patient.

At step 202, the method 200 receives, by the processor 102, medical image data and narrative data of the patient. The medical image data comprises one or more files stored in a digital imaging and communications in medicine (DI-COM) format or common image formats such as a tagged image file format (TIFF), a joint photographic experts group (JPEG), or a portable network graphics (PNG). The medical image data may include whole slide histopathology images, radiological series such as a computed tomography (CT) or a magnetic resonance imaging (MRI), or image tiles derived from whole slide images. The narrative data comprises text-based qualitative input obtained from patient interviews, surveys, clinician notes, or transcribed speech. The acquisition interface accepts inputs via a picture archiving and communication system (PACS) connector, a fast healthcare interoperability resources (FHIR) compliant application programming interface (API), secure file upload, or electronic health record (EHR) integration. The processor 102 maps each received medical image data item and each received narrative data item to the de-identified patient identifier recorded in the mapping table in the memory 104. The processor 102 writes incoming raw data and associated metadata into the memory 104 under controlled access and records receipt events in an audit log.

At step 204, the method 200 preprocesses, by the processor 102, the medical image data and the narrative data by normalizing the medical image data and standardizing the narrative data. The processor 102 implements image normalization by resizing image tensors to fixed dimensions compatible with the ResNet input layer. The processor 102 applies colour or stain normalization for pathology images and intensity scaling as min to max normalization or z-score normalization for radiological images. The processor 102 performs image augmentation during training by applying rotation, scaling or flipping, and by applying other configurable transforms to increase data diversity. The processor 102 implements narrative standardization by tokenizing text into lexical units at word or subword granularity, removing configured stop words, and applying lemmatization to map tokens to canonical forms. The processor 102 optionally performs PHI redaction by replacing identified protected health information tokens with placeholders. The processor 102 stores preprocessed image tensors and standardized narrative tokens in the memory 104 and records preprocessing parameters for reproducibility.

At step 206, the method 200 provides the preprocessed medical image data as inputs to the trained deep residual network to extract one or more quantitative imaging features indicative of the pathological condition. The trained deep residual network comprises the ResNet 50 architecture that includes an input convolutional layer, a series of residual blocks, and identity or projection skip connections. The ResNet 50 residual blocks apply convolution, batch normalization and activation operations to learn residual functions. The processor 102 loads ResNet 50 weights from the memory 104 into the memory for inference. The processor 102 supplies preprocessed image tensors to the ResNet 50 input layer. The processor 102 collects intermediate activations and the pooled output of the final convolutional block. The processor 102 transforms the pooled output through one or more fully connected layers to produce one or more quantitative imaging features represented as fixed-length numeric image feature vectors. The processor 102 normalizes the image feature vectors to a common scale and stores them in the memory 104 for downstream fusion.

At step 208, the method 200 provides the preprocessed narrative data as inputs to the thematic analysis module for extracting one or more thematic codes representing emotional, cognitive or social factors of the patient from the narrative data. The processor 102 executes the thematic analysis module that segments standardized narrative tokens into narrative segments such as sentences or paragraphs. The processor 102 assigns thematic codes to narrative segments using a hybrid coding engine that implements rule-based pattern matching and supervised or unsupervised machine learning models. The coding engine may use transformer encoders or other classifiers. The processor 102 exposes low confidence assignments to the coder adjudication interface, where human coders review and reconcile codes. The processor 102 groups assigned thematic codes into named factors that represent emotional, cognitive or social aspects. The processor 102 computes numeric structured outputs that quantify each named factor using frequency counts, weighted measures or embedding-based aggregation. The processor 102 converts numeric structured outputs into fixed-length theme vectors and stores theme vectors in the memory 104 for fusion.

At step 210, the method 200 fuses vector representations of the one or more quantitative imaging features and the one or more thematic codes into a combined feature vector. The processor 102 aligns image feature vectors and theme vectors using the de-identified patient identifier from the mapping table in the memory 104 to ensure correct pairing by patient and clinical timepoint. The processor 102 implements concatenation in a feature fusion layer to combine normalized image feature vectors and normalized theme vectors into an initial joint representation. The processor 102 applies adaptive weighting by computing learned scalar weights or vector gates using the theme vector as input to a small gating network. The processor 102 multiplies gating outputs element wise with image feature dimensions to emphasize or attenuate particular imaging features based on thematic signals. The processor 102 projects concatenated and weighted inputs through shared neural layers such as fully connected layers or a multilayer perceptron to produce the combined feature vector. The processor 102 persists the combined feature vector in the memory 104 and records fusion parameters.

At step 212, the method 200 provides the combined feature vector as inputs to the integrated diagnostic model configured to generate the multimodal diagnostic output related to the pathological condition of the patient. The processor 102 executes the integrated diagnostic model that comprises a meta classifier or an ensemble program. The ensemble program may include a multilayer perceptron, a gradient boosted tree ensemble, or a stacked ensemble that combines outputs from image only and narrative only classifiers. The processor 102 inputs the combined feature vector to the integrated diagnostic model. The processor 102 obtains a diagnostic classification that indicates presence, subtype or stage of the pathological condition. The processor 102 computes a confidence score that represents calibrated probability for the diagnostic classification. The processor 102 generates a qualitative risk summary that provides narrative driven interpretation including at least one of emotional profile, cognitive profile or social factors of the patient. The processor 102 produces auxiliary interpretability outputs such as saliency maps that map important image regions to feature contributions and natural language snippets that explain how thematic codes influenced the diagnostic score. The processor 102 stores diagnostic outputs and related artifacts in the memory 104 and submits results to the user interface for clinician review.

The method 200 supports receiving the medical image data comprising the plurality of histopathological images and the plurality of radiological images related to the pathological condition including cancer. The processor 102 accepts multiple whole slide images and multiple radiological series per patient. The processor 102 executes modality-specific preprocessing for histopathology by performing stain normalization and tile extraction and executes DICOM series normalization and slice selection for radiology. The method 200 supports receiving the narrative data comprising text based qualitative input from the patient through patient interviews, surveys or other textual information related to patient experiences and perceptions. The processor 102 ingests clinician notes and transcribed interview text through secure channels. The processor 102 timestamps each narrative item and maps narrative items to the de-identified patient identifier in the memory 104 to permit temporal alignment with image data.

The method 200 supports preprocessing the medical image data by image resizing and image augmentation that includes at least one of rotation, scaling or flipping. The processor 102 implements resizing routines to produce tensor dimensions compatible with the ResNet 50 input. The processor 102 applies configurable augmentation policies that include rotation, scaling and flipping during model training. The processor 102 records augmentation parameters in the memory 104 and uses augmented examples to improve the generalization of the ResNet based imaging module.

The method 200 supports standardizing the narrative data by tokenizing the narrative data, removing stop words and lemmatizing the narrative data. The processor 102 executes tokenization routines to split narrative text into tokens. The processor 102 removes stop words according to configurable stop word lists. The processor 102 applies lemmatization to map inflected tokens to canonical lemmas. The processor 102 stores standardized tokens and mapping information in the memory 104 for use by the thematic analysis module.

The method 200 supports a trained deep residual network that comprises the ResNet 50 architecture including the plurality of residual connections configured to learn one or more residual functions by applying the sequence of operations including convolution, batch normalization and activation. The processor 102 executes the ResNet 50 inference pipeline to propagate preprocessed image tensors through convolutional filters and residual blocks. The processor 102 extracts intermediate activations and produces image feature vectors that represent learned hierarchical visual features indicative of pathological conditions.

The method 200 supports thematic coding steps where the processor 102 labels one or more narrative segments of the narrative data with the one or more thematic codes. The processor 102 groups the one or more thematic codes into one or more emotional, cognitive or social factors of the patient. The processor 102 generates one or more structured outputs that quantify the one or more emotional, cognitive or social factors. The processor 102 vectorizes the one or more structured outputs for the fusion. The thematic analysis module provides automated coding and human adjudication workflows. The processor 102 computes theme scores using counting, weighting or embedding aggregation. The processor 102 converts numeric structured outputs into fixed length theme vectors that are compatible with image feature vectors for subsequent fusion.

The method 200 supports fusing by concatenating vector representations of the one or more quantitative imaging features and the one or more thematic codes in a feature fusion layer. The processor 102 applies adaptive weighting of the one or more quantitative imaging features and the one or more thematic codes. The processor 102 aligns the one or more quantitative imaging features and the one or more thematic codes using the common patient identifier. The processor 102 fuses the vector representations through a shared neural layer. The processor 102 implements the feature fusion layer, the gating network that computes adaptive weights, and the shared neural layer that projects concatenated inputs into a combined feature vector used by the integrated diagnostic model.

The method 200 supports producing multimodal diagnostic output that comprises at least one of a diagnostic classification including presence, subtype or stage of the pathological condition, the confidence score, or the qualitative risk summary including the narrative-driven interpretation indicating at least one of emotional profile, cognitive profile or social factors of the patient. The processor 102 formats diagnostic classification outputs for clinical consumption and includes interpretability cues that show the top contributing thematic codes and the image regions associated with high feature importance.

The method 200 supports pre-training the trained deep residual network on a generic image dataset and fine-tuning on medical imaging data to extract one or more quantitative imaging features. The processor 102 initializes ResNet 50 weights from a generic image dataset such as ImageNet. The processor 102 fine-tunes one or more layers of ResNet 50 using labeled domain specific medical imaging data. The processor 102 uses transfer learning techniques including differential learning rates and class weighting during fine-tuning.

The method 200 supports receiving a clinical diagnostic outcome of the patient and updating at least one of the trained deep residual network or the thematic analysis module based on the clinical diagnostic outcome. The processor 102 receives confirmed clinical outcomes through secure interfaces. The processor 102 validates and curates incoming labels and schedules retraining, recalibration or threshold adjustments for the ResNet based imaging module or for classifiers used in the thematic analysis module. The processor 102 records model update operations and retains prior model versions in the memory 104 for regulatory traceability.

The method 200 supports training and validating the integrated diagnostic model in the simulation environment by generating the plurality of synthetic histopathological images using the generative adversarial network trained on the plurality of domain specific medical images, by generating synthetic narrative data using the natural language generation model trained on domain specific patient narratives, and by evaluating performance of the integrated diagnostic model comprising the meta classifier or the ensemble program using at least one performance metric selected from accuracy, precision, recall, F1 score, thematic coherence and thematic relevance. The processor 102 trains the GAN using domain specific medical images to produce synthetic tiles for large scale experiments. The processor 102 trains the NLG model on the identified narrative corpora to produce synthetic narratives that emulate clinician-reviewed themes. The processor 102 evaluates the integrated diagnostic model on combined synthetic and real hold out sets using the recited metrics and stores evaluation outcomes in the memory 104 for model selection.

Variations and alternative embodiments are supported. The ResNet 50 may be replaced with other residual or non residual backbones. The thematic analysis module may use manual coding or fully automated transformer based coding. Fusion may be early, late or hybrid. Synthetic data generation may use conditional GANs or other generative models. The integrated diagnostic model may be a single classifier or an ensemble. Each variation retains alignment and fusion of image and theme vectors to produce the combined feature vector and the multimodal diagnostic output.

Figure 3:
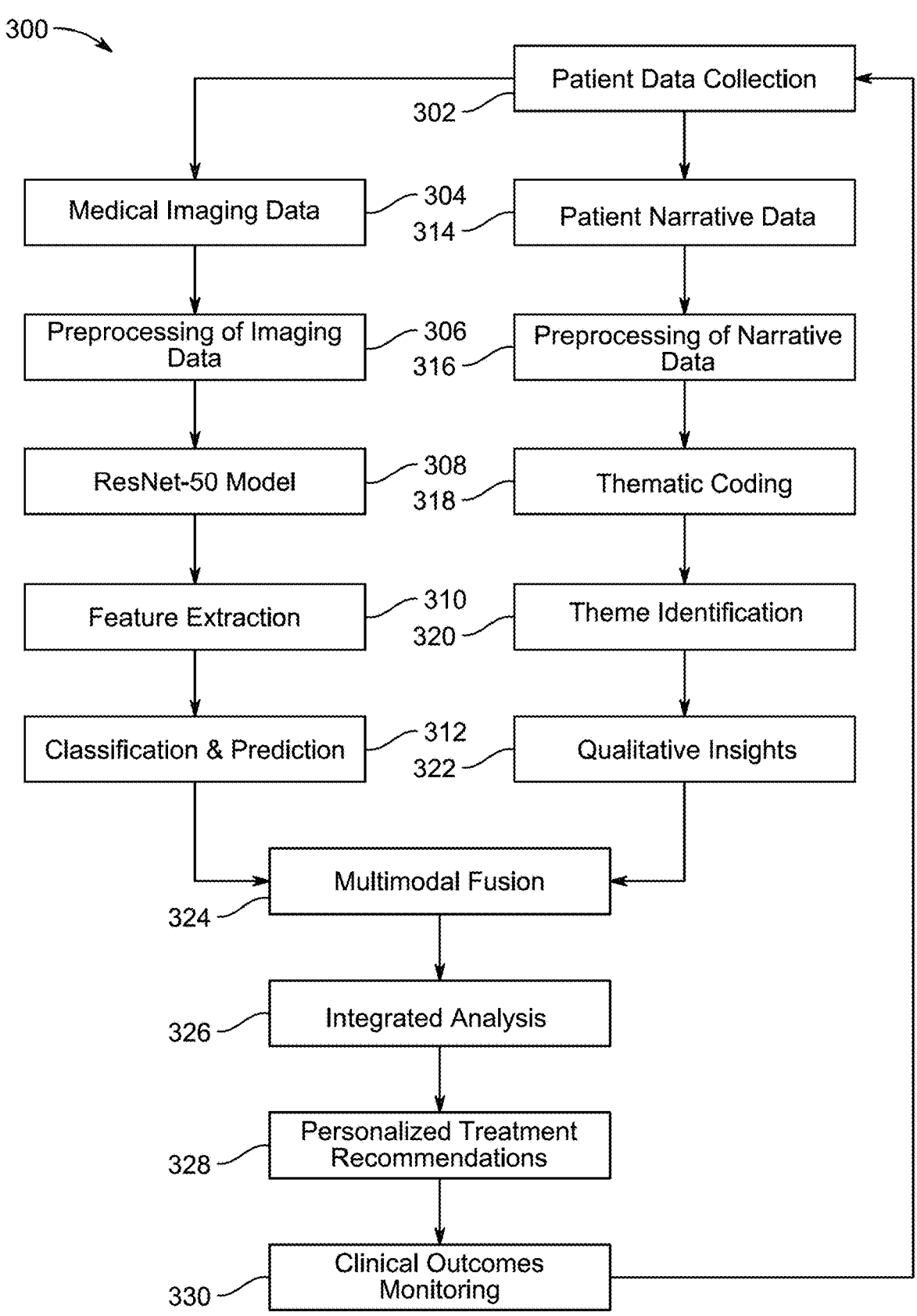
FIG. 3 illustrates a flow diagram for the distinct data pathways and their integration, in accordance with the present invention, according to an embodiment of the present invention.

FIG. 3 illustrates a flow diagram 300 for the distinct data pathways and their integration, in accordance with the present invention.

At block 302, the method initiates with the collection of patient data. The patient data comprises medical imaging data and patient narrative data.

At block 304, the medical imaging data collected in block 200 is directed to the imaging analysis pathway.

At block 306, the imaging data undergoes preprocessing to prepare it for feature extraction. The preprocessing steps include resizing images to fixed dimensions, normalizing intensity values, and applying stain normalization for histopathological images.

At block 308, the preprocessed images are supplied to a ResNet-50 deep residual network. The ResNet-50 comprises stacked residual blocks with skip connections, allowing the network to learn residual mappings efficiently.

At block 310, the ResNet-50 model outputs quantitative imaging features that characterize the underlying pathological condition. These features include patterns, textures, and structures indicative of cancer presence, subtype, or progression stage. The extracted features are converted into numeric feature vectors stored for downstream fusion.

At block 312, the extracted imaging features are used for classification and prediction. The processor applies classification layers or ensemble classifiers to predict diagnostic outcomes such as the presence or absence of cancer, cancer subtype, or progression stage. Confidence scores may also be generated to quantify the reliability of predictions.

At block 314, the patient narrative data collected at block 200 is directed to the narrative analysis pathway. The narrative data provides insights into the patient's lived experience, including emotional, cognitive, and social dimensions, and is critical for generating a holistic diagnostic interpretation.

At block 316, the narrative data undergoes preprocessing. The steps include tokenization of textual input, removal of stop words, and lemmatization to reduce words to their canonical forms. These steps ensure consistency and reduce noise in the data prior to thematic coding.

At block 318, the preprocessed narrative segments are subjected to thematic coding. Thematic codes are assigned to meaningful segments of the narrative to capture key concepts, including emotional states, cognitive perceptions, and social concerns. The processor 102 may use rule-based systems or machine learning classifiers for this task, optionally supported by coder adjudication.

At block 320, the thematic codes are grouped into higher-level themes representing emotional, cognitive, or social factors. These themes reflect the patient's psychological and social context, which may impact disease management and treatment adherence. Structured theme vectors are generated to quantify each identified theme.

At block 322, the identified themes are converted into qualitative insights that summarize the patient's perspective. These insights may describe the patient's emotional resilience, cognitive outlook, or social support systems.

At block 324, Multimodal Fusion, quantitative imaging features from the ResNet-50 path and thematic vectors from the thematic analysis path are aligned using the de-identified patient identifier. The processor 102 concatenates the vectors and applies adaptive weighting to balance contributions from both modalities. Fusion is performed through a shared neural layer to generate a combined feature vector representing both clinical imaging evidence and patient narrative context.

At block 326, the combined feature vector is processed by the integrated diagnostic model, which may include a meta-classifier or ensemble system. The model analyzes the fused multimodal data to provide a diagnostic inference, integrating both quantitative and qualitative perspectives.

At block 328, the integrated analysis results are translated into personalized treatment recommendations. The recommendations consider imaging-based diagnostic predictions as well as patient-specific thematic insights to align treatment strategies with precision medicine principles. The recommendations may include suggested therapies, monitoring protocols, or supportive care options.

At block 330, the method 300 monitors clinical outcomes after treatment implementation. Patient responses, both biomedical and narrative, are collected and reintroduced into the model to refine predictions and improve personalization. This establishes a feedback loop that ensures adaptability and continuous learning of the diagnostic system in real-world clinical practice.

Figure 4:
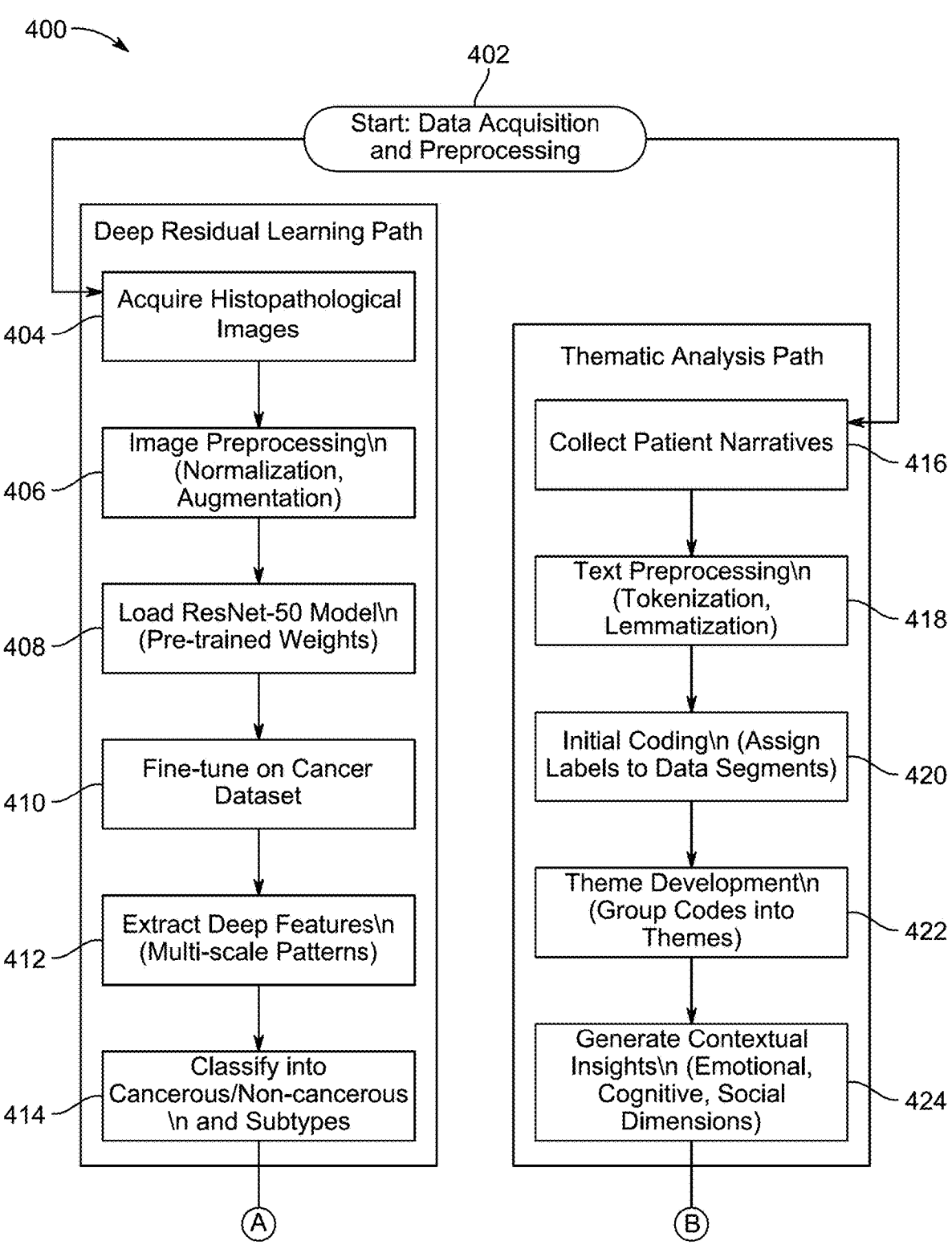
FIG. 4 illustrates a flow diagram of the proposed methodology for integrating deep residual learning (DRL) with thematic analysis (TA) for cancer diagnostics and treatment planning, according to an embodiment of the present invention.
Figure 4:
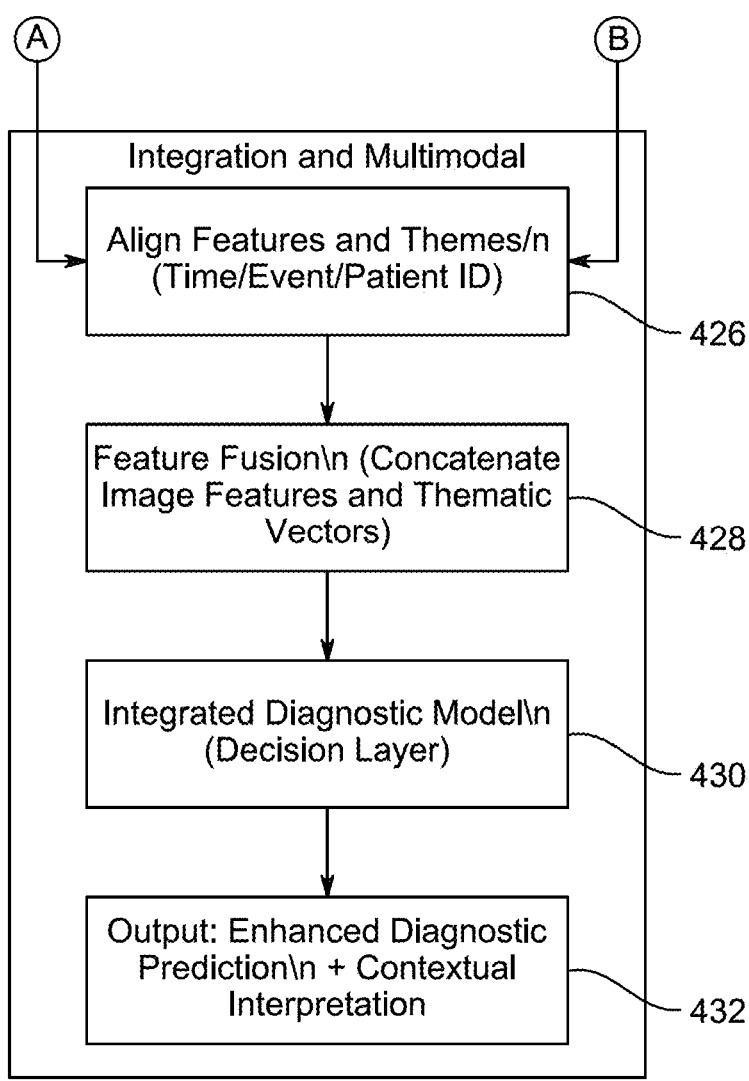

FIG. 4 illustrates a flow diagram 400 of the proposed methodology for integrating deep residual learning (DRL) with thematic analysis (TA) for cancer diagnostics and treatment planning. The figure highlights three interconnected paths: the deep residual learning path, the thematic analysis path, and the integration and multimodal fusion layer, each of which contributes to a comprehensive diagnostic framework.

Block 402: Start data acquisition and preprocessing.

Histopathological or radiological images associated with a suspected cancer case are acquired. These images undergo normalization and augmentation. Normalization ensures consistent pixel intensity distributions. Augmentation, such as rotation, flipping, or scaling, enhances dataset diversity, thereby reducing overfitting and improving generalization during training.

Deep Residual Learning Path

Block 404: Acquire Histopathological Images

At this stage, histopathological or radiological images related to the patient's suspected condition are acquired. These medical imaging inputs serve as the foundation for quantitative analysis of cancer presence and subtypes.

Block 406: Image Preprocessing (Normalization, Augmentation)

The acquired images undergo preprocessing to enhance quality and consistency.

Normalization ensures pixel intensity consistency, while augmentation (e.g., rotation, scaling, flipping) increases dataset diversity.

Block 408: Load ResNet-50 Model (Pre-trained Weights)

A deep residual network (ResNet-50) model is employed. Its pre-trained weights, usually derived from large datasets, provide an initialization for medical imaging tasks.

Block 410: Fine-tune on Cancer Dataset

The pre-trained ResNet-50 model is fine-tuned using domain-specific cancer datasets. This step adapts the general features learned during pre-training to the specific task of cancer detection and classification.

Block 412: Extract Deep Features (Multiscale Patterns)

The model extracts multi-scale deep features from the imaging data. These features include patterns indicative of cancerous and non-cancerous tissues, as well as cancer subtypes.

Block 414: Classify into Cancerous/Non-Cancerous and Subtypes

Based on the extracted features, the system 100 classifies the images into categories such as cancerous versus non-cancerous, and further into subtypes of cancer.

This provides early and accurate diagnostic outcomes.

Thematic Analysis Path

Block 416: Collect Patient Narratives

Patient narratives, such as interviews, surveys, or self-reported experiences, are collected to provide qualitative insight into the patient's perspective.

Block 418: Text Preprocessing (Tokenization, Lemmatization)

The narrative data undergoes preprocessing to prepare it for structured analysis. This includes tokenization (splitting text into units) and lemmatization (converting words to their base forms).

Block 420: Initial Coding (Assign Labels to Data Segments)

The processed text is coded by assigning labels to different segments, representing recurring ideas or phenomena in the narratives.

Block 422: Theme Development (Group Codes into Themes)

The assigned codes are aggregated into broader themes such as emotional responses, coping strategies, or perceptions of care, which highlight significant aspects of patient experience.

Block 424: Generate Contextual Insights (Emotional, Cognitive, Social Dimensions)

From the identified themes, contextual insights are generated. These insights capture patient experiences across emotional, cognitive, and social dimensions, providing a holistic view of the patient's condition.

Integration and Multimodal Fusion Layer

Block 426: Align Features and Themes (Time/Event/Patient ID)

The quantitative features from the DRL path and qualitative themes from the TA path are aligned based on patient identifiers, time of collection, or clinical events.

Block 428: Feature Fusion (Concatenate Image Features and Thematic Vectors)

A multimodal fusion step is performed, where the extracted image features and thematic vectors are concatenated into a unified representation.

Block 430: Integrated Diagnostic Model (Decision Layer)

The fused data is processed through an integrated diagnostic model. This model serves as the decision layer, applying machine learning or deep learning algorithms to predict diagnostic outcomes.

Block 432: Output: Enhanced Diagnostic Prediction+Contextual Interpretation

The final output consists of enhanced diagnostic predictions supplemented with contextual interpretations. This dual outcome improves diagnostic accuracy while also incorporating patient-centered insights, thereby facilitating personalized treatment planning and improved adherence.

Experiments

A simulation-based methodology is employed to validate the integration of the DRL and the TA for cancer diagnostics in a controlled environment prior to clinical deployment. The simulation environment enables systematic testing of the proposed system, ensuring robustness, reproducibility, and readiness for clinical application. The methodology provides a structured framework to generate synthetic datasets, train multimodal models, evaluate diagnostic performance, and establish reliability across diverse scenarios.

In an embodiment, a simulation environment and computational infrastructure are established to enable high fidelity testing. The environment comprises computing nodes with graphics processing units (GPUs) or neural accelerators for deep learning tasks, together with secure data storage for imaging datasets, narrative corpora, and trained models. Synthetic medical imaging data is generated using generative adversarial networks (GANs) trained on existing histopathological and radiological datasets to produce realistic cancer images with variations in morphology and staging. Synthetic patient narratives are created using natural language generation models trained on de-identified transcripts, thereby simulating diverse linguistic patterns and emotional expressions representative of real patient experiences.

In an embodiment, the training and evaluation of models is conducted using the synthetic and real datasets. The DRL component is trained on the imaging data with techniques such as augmentation, regularization, and early stopping to enhance generalization. The TA component processes synthetic narratives to identify initial codes, group them into themes, and generate structured representations of psychosocial and cognitive dimensions. The integration of imaging and textual features is performed through a multimodal fusion mechanism, and the combined diagnostic model is validated using classification metrics, including accuracy, precision, recall, and F1 score for cancer detection, as well as thematic coherence and relevance for narrative interpretation. Cross-validation techniques are employed to assess reliability across multiple simulated scenarios.

In an embodiment, the deep learning model employed for image analysis is based on the ResNet-50 architecture, a 50-layer convolutional neural network designed with residual skip connections to mitigate vanishing gradient problems. ResNet-50 is initialized with pre-trained weights obtained from large-scale datasets such as ImageNet and subsequently fine-tuned on cancer-specific imaging data. This enables the extraction of high-level and multi-scale features critical for distinguishing between benign and malignant tissues. The network architecture includes convolutional blocks, identity mappings, batch normalization, and activation layers, followed by average pooling and fully connected classification layers with softmax output. Data augmentation techniques such as rotation, flipping, and scaling are applied during training to improve robustness, and transfer learning is leveraged for faster convergence.

In an embodiment, thematic analysis is implemented to process patient-generated narrative data and extract qualitative insights. Thematic analysis follows a rigorous six-phase approach comprising familiarization with the dataset, generation of initial codes, searching for themes, reviewing themes, defining and naming themes, and producing structured reports. The process identifies overarching themes such as resilience, fatigue, fear of recurrence, or reliance on social support, which reflect the emotional, cognitive, and social dimensions of cancer patients. These themes are converted into structured outputs, including numeric representations such as prevalence scores or embeddings, to enable integration with quantitative image features.

In an embodiment, parameter selection is guided by theoretical justifications and empirical evidence. For the DRL path, parameters include a learning rate of 0.001 to balance convergence speed and stability, a batch size of 32 for computational efficiency and gradient reliability, the Adam optimizer for adaptive updates, and training over approximately 50 epochs with early stopping to reduce overfitting. Data augmentation techniques are consistently applied to ensure diversity in the training data. For the TA path, an inductive coding approach is adopted to allow themes to emerge organically from narratives. Thematic saturation is ensured to capture comprehensive patient experiences. Inter-coder reliability is enforced by having multiple coders independently label data and reconcile any differences. Qualitative analysis software is employed to systematically organize and analyze codes and themes.

In an embodiment, ablation studies and sensitivity analyses are conducted within the simulation environment to measure the impact of different parameters and strategies on performance. The processor 102 executes controlled experiments varying DRL hyperparameters, TA coding thresholds, and multimodal fusion techniques to evaluate diagnostic accuracy and thematic coherence. Additional experiments assess fairness, generalizability, and resilience to domain shifts across simulated populations.

In an embodiment, the simulation methodology enforces strict privacy and security standards. All synthetic datasets are validated to exclude re-identifiable patient information, and de-identification processes are applied consistently. Access control, logging, and auditing mechanisms are employed to ensure regulatory compliance. Clinician reviews are incorporated to validate the plausibility and relevance of synthetic data before it is included in training or evaluation.

In an embodiment, the simulation-based methodology provides a reproducible, auditable, and secure platform for developing and validating the integrated DRL and TA diagnostic system. Further, in an embodiment, results and analytical validation of the system integrating the DRL and the TA are obtained through the simulation-based method 200 described above. The evaluation establishes both the quantitative performance of the DRL component and qualitative insights derived from the TA component.

In an embodiment, the DRL model based on the ResNet-50 architecture is trained on a synthetic dataset comprising histopathological images representing multiple types and stages of cancer. The performance of the DRL model is validated using standard classification metrics. The model achieves an accuracy of 99.27%, demonstrating its ability to correctly classify a majority of input images. Precision is measured at 99.44%, confirming the capability of the system 100 to correctly identify cancer-positive samples while minimizing false positives. Recall is measured at 98.56%, establishing the ability of the system 100 to detect most of the actual positive cases without significant misses. An F1 score of 99.00% is recorded, balancing both precision and recall and confirming the diagnostic capability of the DRL model. These results highlight the suitability of the DRL component for early detection and accurate classification of cancer, ensuring a high level of clinical confidence.

In an embodiment, the TA component analyzes synthetic patient narratives to extract meaningful qualitative insights. The analysis identifies recurring themes that are significant in the cancer diagnostic journey. Emotional responses such as anger and sadness are identified, reflecting the psychological burden faced by patients. Cognitive processing is observed to be diminished, with lower scores in insight and causality, indicating that patients often struggle to make sense of their illness. Social dynamics emerge as a critical theme, with patients expressing the importance of relationships, shared decision-making, and reliance on support networks. These qualitative insights provide a deeper understanding of patient experiences, complementing the quantitative accuracy of the DRL model and enabling the system to align diagnostic outcomes with patient-centered perspectives.

In an embodiment, the fusion of DRL and TA demonstrates the advantage of combining quantitative medical imaging features with qualitative narrative insights. The integrated framework ensures that diagnostic predictions are not only precise but also contextually enriched by patient perspectives. This comprehensive approach has potential to improve diagnostic accuracy, personalize treatment recommendations, and increase patient satisfaction and adherence to treatment plans.

Figure 5:
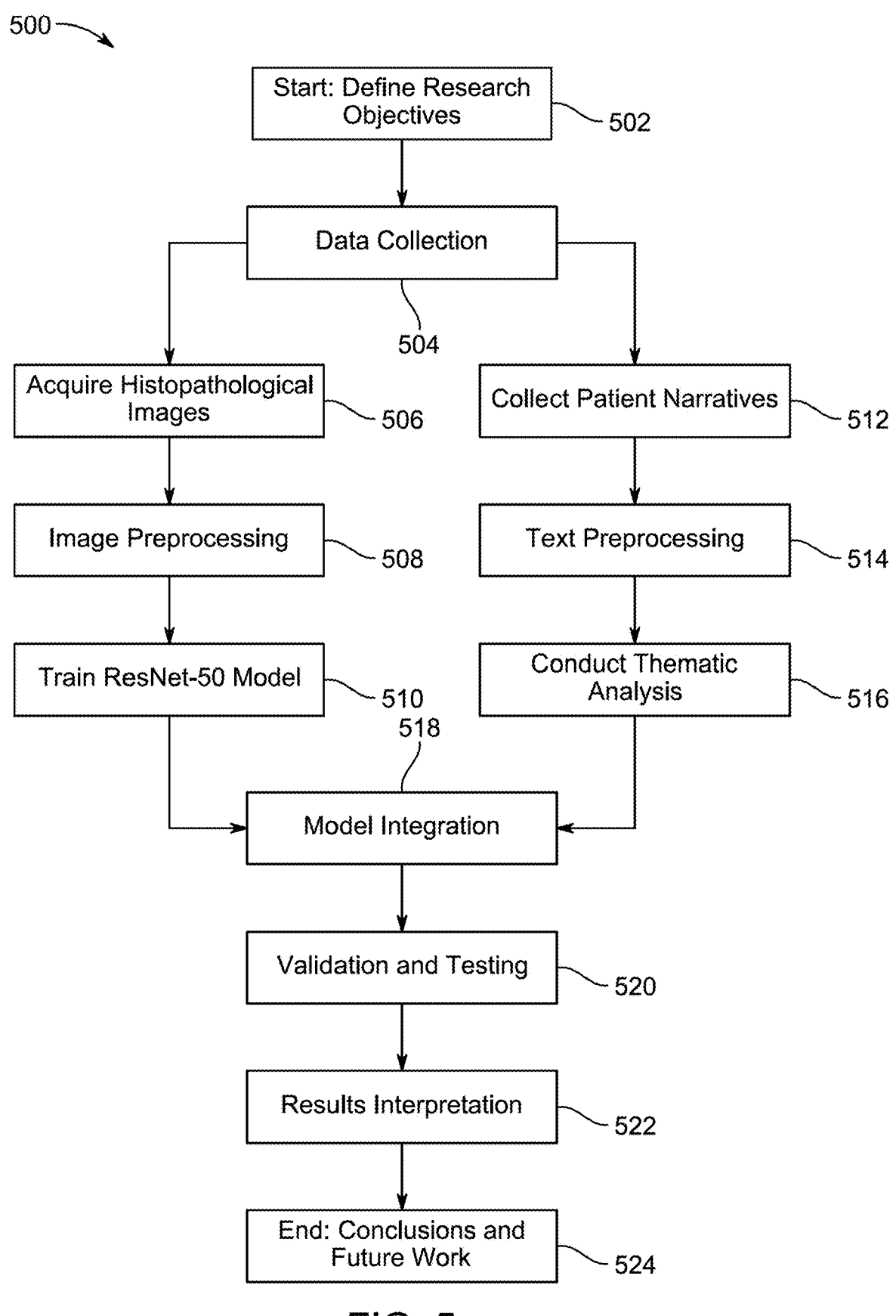
FIG. 5 illustrates a flow diagram of deep residual learning and thematic analysis in cancer diagnostics, according to an embodiment of the present invention.

FIG. 5 illustrates a flow diagram 500 of deep residual learning and thematic analysis in cancer diagnostics. The flowchart provides a sequential depiction of the methodology by presenting the DRL path and TA path in parallel, followed by their integration in a multimodal fusion layer.

Block 502: The methodology initiates with a step of defining research objectives, wherein specific objectives are established with a focus on enhancing diagnostic accuracy by employing both DRL and TA methodologies.

Block 504: Data collection. In the subsequent step of data collection, a comprehensive dataset of histopathological images is obtained, the dataset being representative of diverse cancer types and stages. Alongside, detailed patient narratives are gathered to capture subjective experiences and provide insights into the diagnosis.

The methodology then proceeds to data preprocessing. In relation to imaging data, preprocessing includes normalization, resizing, and augmentation to prepare the images for robust training of the model. In relation to textual data, preprocessing comprises tokenization, stop-word removal, and lemmatization, thereby structuring the narratives for efficient thematic analysis.

Block 506: Acquire Histopathological Images. Clinical histopathological images are obtained from hospital datasets, research archives, or repositories to serve as structured input for DRL analysis.

Block 508: Image Preprocessing. The acquired images are subjected to preprocessing steps such as normalization, resizing, contrast enhancement, and noise reduction to ensure consistency for deep learning.

Block 510: Train ResNet-50 Model. A ResNet-50 architecture is trained on the preprocessed image dataset, enabling automated extraction of hierarchical deep features relevant to cancer classification and related tasks.

Block 512: Collect Patient Narratives. Patient-generated data, such as interviews, transcripts, or clinical reports, is collected to capture personal experiences, emotional states, and social contexts.

Block 514: Text Preprocessing. The narratives are preprocessed to remove stopwords, standardize terms, and tokenize text, thereby preparing unstructured input for thematic analysis.

Block 516: Conduct Thematic Analysis. The preprocessed narratives undergo thematic analysis, which identifies recurring themes and constructs (e.g., emotional, cognitive, social dimensions) that complement clinical data.

Block 518: Model integration. A subsequent step of model integration is executed, wherein the outputs generated from the DRL model and the TA are combined. The integration yields a comprehensive diagnostic framework that leverages both objective imaging data and subjective patient insights.

Block 520: Validation and testing. Following integration, a validation and testing step is performed to evaluate the accuracy, robustness, and reliability of the combined methodology.

Block 522: Results interpretation. Thereafter, a step of results interpretation is undertaken, wherein the outcomes are analyzed to assess the effectiveness of the integrated approach, identifying strengths, limitations, and potential areas for refinement.

Block 524: Conclusions and future work. The methodology concludes with a step directed to conclusions and future work. This step summarizes the key findings and outlines prospective research directions aimed at further advancing cancer diagnostics through the synergistic use of deep residual learning and thematic analysis.

Figure 6:
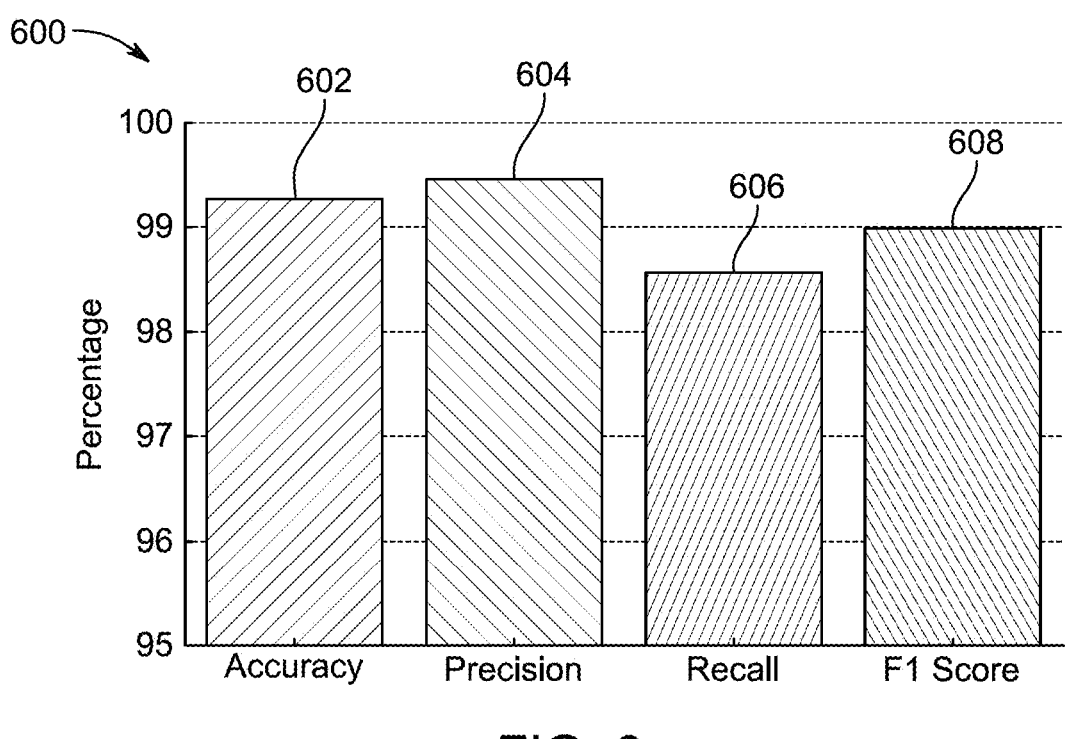
FIG. 6 is a bar chart diagram illustrating performance metrics of a ResNet-50 model, in accordance with an embodiment of the present disclosure, according to an embodiment of the present invention.

FIG. 6 is a bar chart diagram 600 illustrating the performance metrics of a ResNet-50 model, in accordance with an embodiment of the present disclosure. The bar chart diagram 600 provides a quantitative assessment of the model's classification efficacy, particularly in the domain of cancerous tissue identification. The vertical axis represents percentage values from 95% to 100%, while the horizontal axis delineates four distinct performance metrics.

The first bar 602, represents the accuracy of the model. This metric, indicating a value of approximately 99.25%, is defined as the ratio of correctly classified instances to the total number of instances. It serves as a general measure of the model's correctness across all classes.

The second bar 604, represents the precision of the model. This metric, indicating a value of approximately 99.45%, is defined as the ratio of true positive classifications to the total number of instances classified as positive (i.e., true positives plus false positives). This metric quantifies the reliability of a positive classification.

The third bar 606, represents the recall of the model. This metric, indicating a value of approximately 98.55%, is defined as the ratio of true positive classifications to the total number of actual positive instances (i.e., true positives plus false negatives). This metric quantifies the model's ability to identify all relevant instances.

The fourth bar 608, represents the F1 Score of the model. This metric, indicating a value of approximately 99.0%, is computed as the harmonic mean of Precision and Recall. It provides a balanced measure of the model's performance, particularly in cases of class imbalance.

Figure 7:
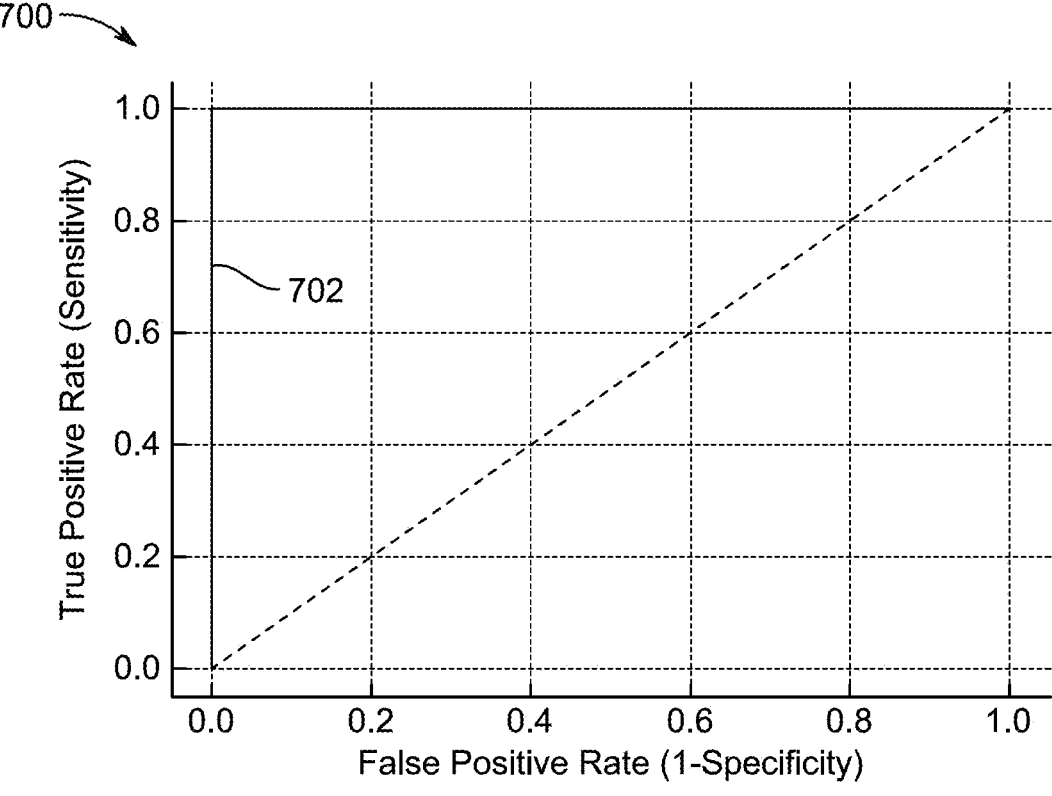
FIG. 7 is a graphical representation of a receiver operating characteristic (ROC) curve for the ResNet-50 model performance, according to an embodiment of the present invention.

FIG. 7 is a graphical representation 700 of a receiver operating characteristic (ROC) curve for the ResNet-50 model performance, in accordance with an embodiment of the present disclosure, offering a comprehensive graphical representation of its diagnostic ability to discriminate between classes (e.g., cancerous and non-cancerous tissues) across all classification thresholds.

The vertical axis represents the true positive rate (TPR), also known as Sensitivity. It measures the proportion of actual positive cases that the model correctly identifies. A higher TPR indicates the model is effective at detecting the condition when it is present.

The horizontal axis represents the false positive rate (FPR), which is calculated as 1 minus Specificity. The FPR measures the proportion of actual negative cases that are incorrectly classified as positive. A lower FPR is desirable, as it signifies fewer false alarms.

The line 702 is the model's ROC curve. Its path illustrates the trade-off between the True Positive Rate and the False Positive Rate at various threshold settings. An ideal curve "hugs" the top-left corner of the plot, which represents a high TPR and a low FPR. The curve in FIG. 7 shows a perfect performance, immediately achieving a TPR of 1.0 while maintaining an FPR of 0.0.

The dashed diagonal line extending from (0,0) to (1,1) signifies the performance of a classifier with no discriminative capability, indicative of random guessing. Any model whose curve lies below this line is performing worse than the baseline.

The most critical metric shown is the area under the curve (AUC), which is provided in the legend as AUC=1.00. The AUC value serves as a single scalar summary of the model's performance. It represents the probability that the model will rank a randomly chosen positive instance higher than a randomly chosen negative one. An AUC of 1.0 signifies a perfect classifier. This means the model can flawlessly distinguish between the positive and negative classes. For every possible threshold, the model correctly classifies all instances.

In conclusion, the ROC curve in FIG. 7 demonstrates that the ResNet-50 model exhibits ideal diagnostic performance, achieving perfect classification accuracy with no trade-off between sensitivity and specificity.

Figure 8:
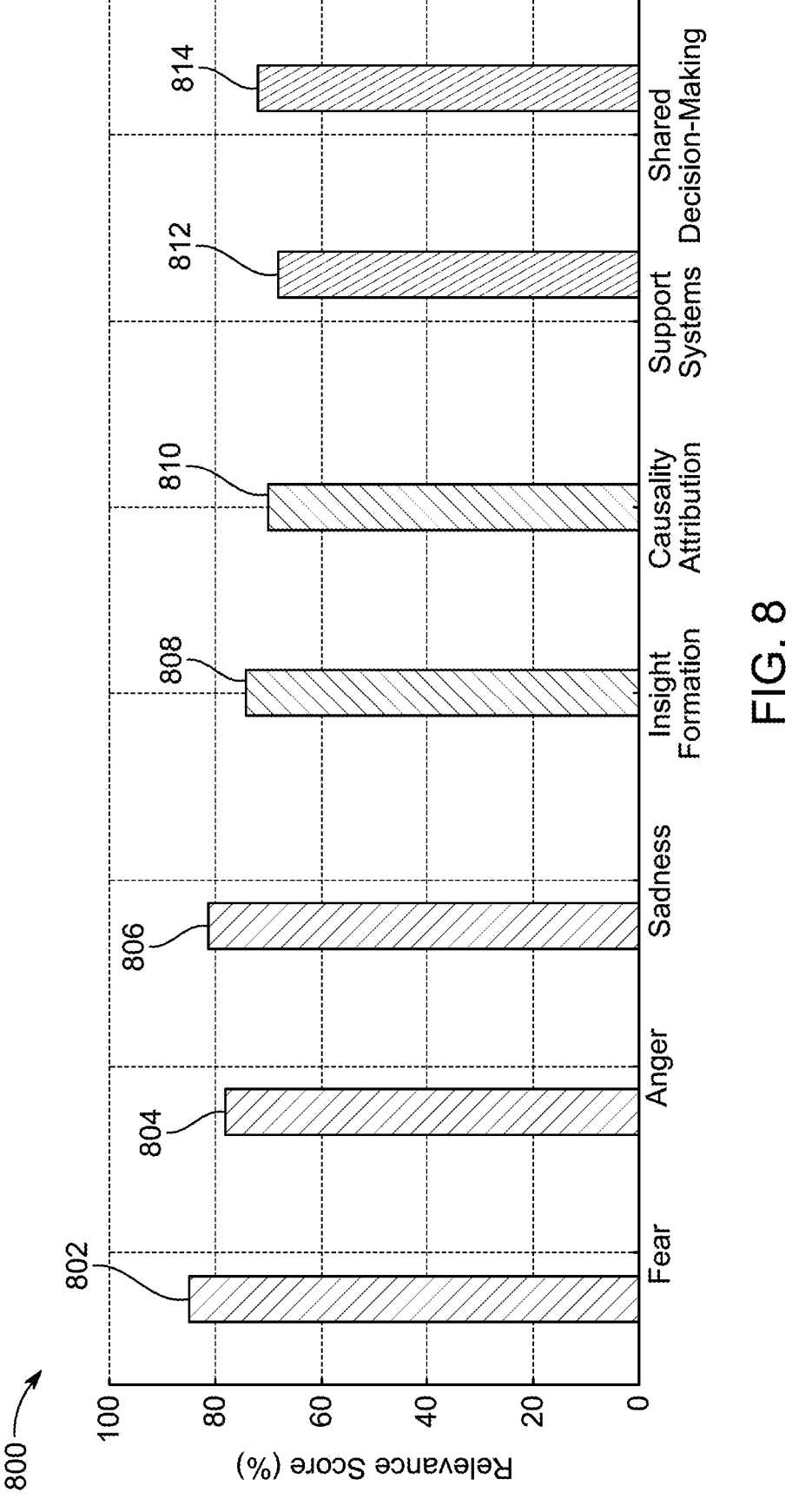
FIG. 8 is a bar chart that represents thematic insights from patient narratives, according to an embodiment of the present invention.

FIG. 8 is a bar chart 800 that represents thematic insights from patient narratives, in accordance with an embodiment of the present disclosure. The chart categorizes these themes into emotional, cognitive, and social dimensions, with the vertical axis representing a relevance score as a percentage. This format offers a clear comparison across different aspects of the patient experience.

The themes are detailed as follows:

Emotional Themes:

This category encompasses themes that are prevalent in patients' initial reflections on their diagnosis.

802 (Fear): The first bar represents the theme of Fear, which has the highest relevance score in this category at approximately 85%.

804 (Anger): The second bar represents Anger, showing a relevance score of approximately 78%.

806 (Sadness): The third bar represents Sadness, with a relevance score of approximately 81%.

Cognitive Themes:

This category includes themes related to patients' meaning-making processes following a diagnosis.

808 (Insight Formation): This bar represents Insight Formation, indicating a relevance score of approximately 74%.

810 (Causality Attribution): This bar represents Causality Attribution, which has a relevance score of approximately 70%.

Social Themes:

This category highlights the relational context in which patients process their diagnosis and make decisions.

812 (Support Systems): This bar represents the importance of Support Systems, with a relevance score of approximately 68%.

814 (Shared Decision-Making): The final bar represents Shared Decision-Making, showing a relevance score of approximately 72%.

Collectively, this visualization demonstrates a comprehensive methodology, combining deep qualitative insights with quantitative analysis to better understand the patient experience in cancer diagnostics.

Figure 9:
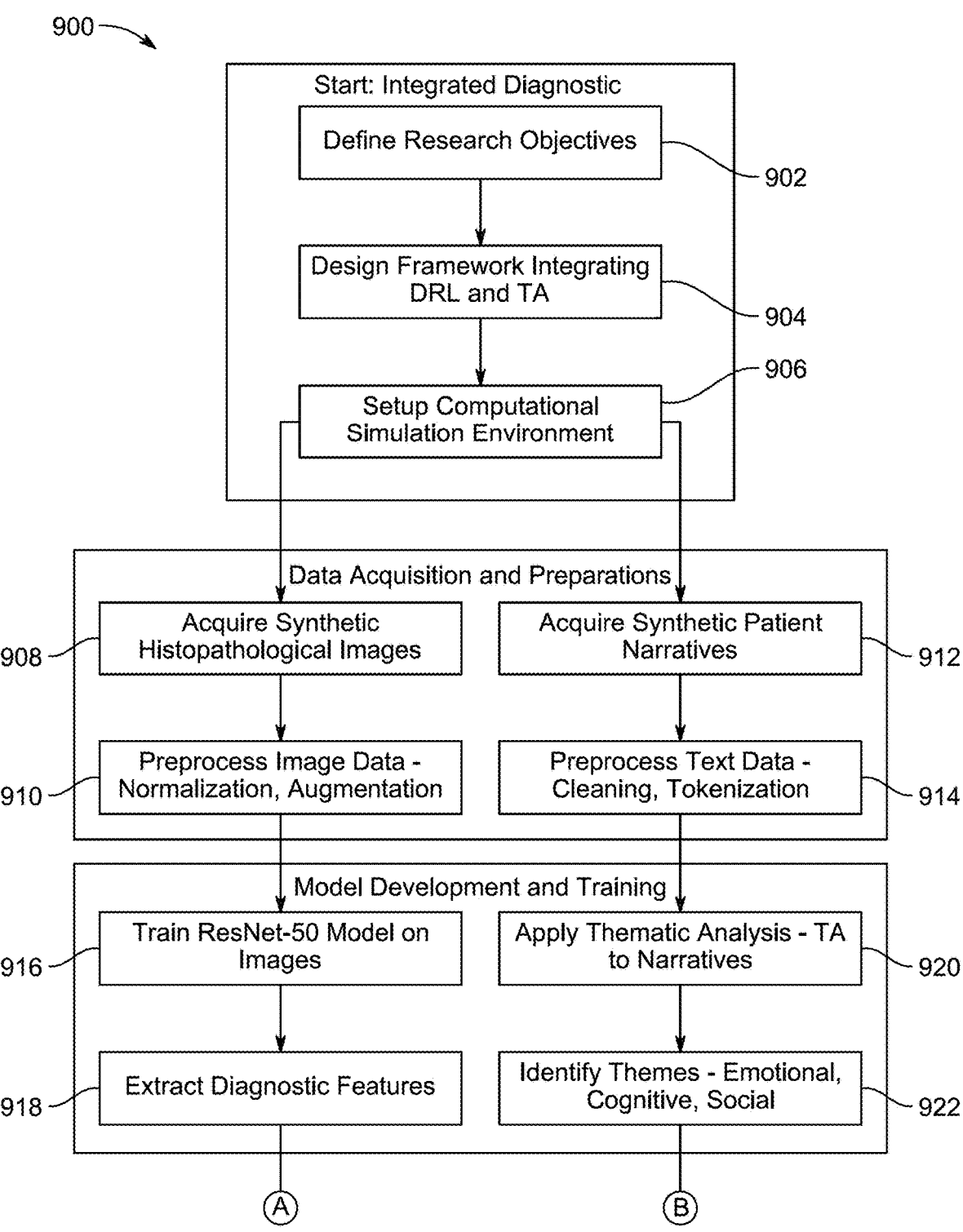
FIG. 9 discloses a flow diagram of the integrated diagnostic methodology, according to an embodiment of the present invention.
Figure 9:
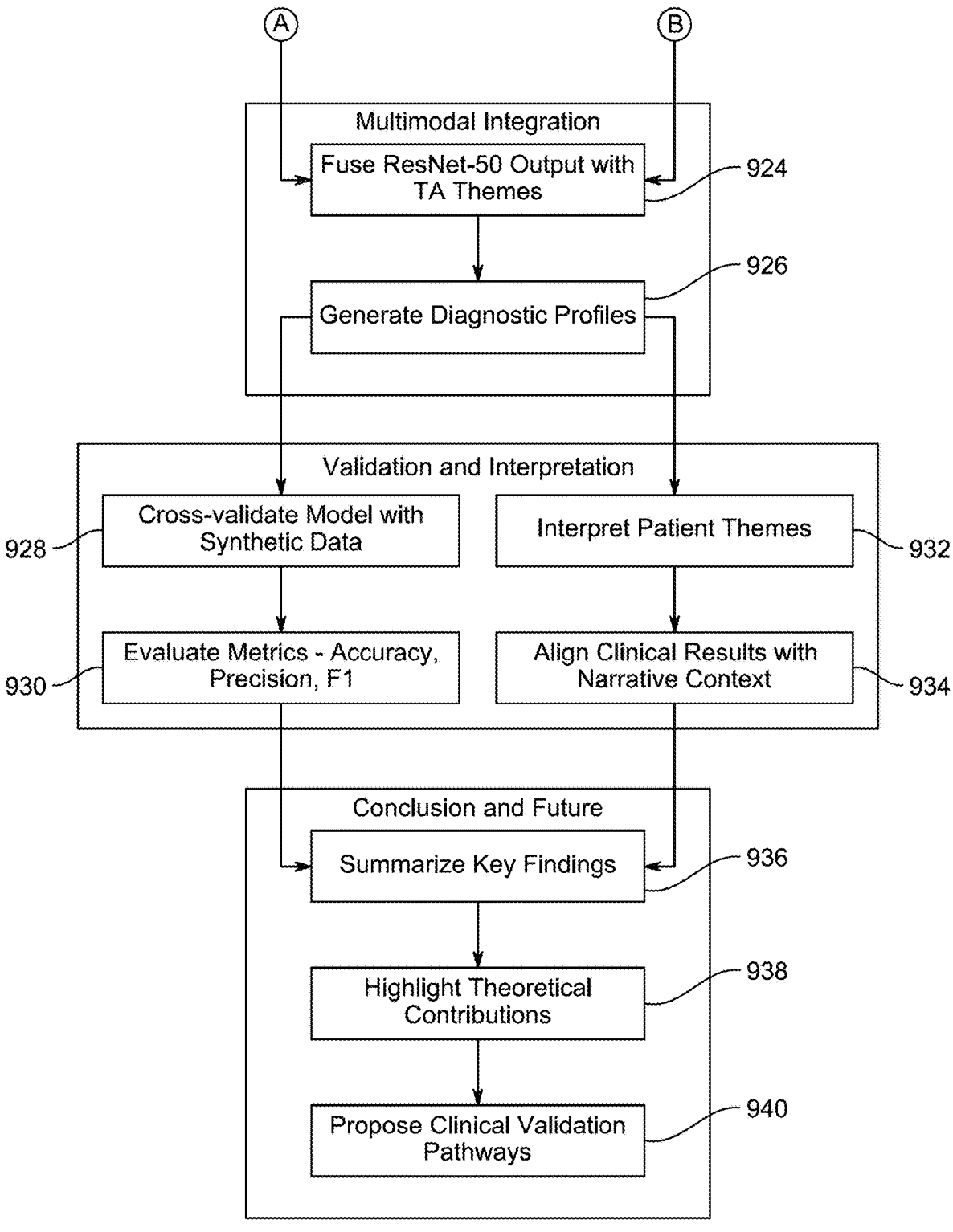

FIG. 9 discloses a flow diagram 900 of the integrated diagnostic methodology, capturing the detailed workflow of the integrated framework that combines the deep residual learning (DRL) and the thematic analysis (TA) for cancer diagnostics. The flowchart provides an end-to-end representation of the diagnostic pipeline, beginning with research objectives and culminating in validation and future directions.

Integrated Diagnostic

Block 902: Define Research Objectives. Clear objectives are established to improve cancer diagnostic accuracy by integrating DRL with TA. This step sets the foundation for both technical and patient-centered dimensions of the framework.

Block 904: Design Integrated Framework. The architecture of the framework is designed to combine ResNet-50 for imaging data with thematic analysis for narrative data. The design ensures parallel yet convergent paths.

Block 906: Setup Simulation Environment. A computational environment is configured, enabling high-performance data processing, model training, and integration of multimodal results.

Data Acquisition and Preprocessing

Block 908: Acquire Synthetic Histopathological Images. Structured imaging data is acquired to represent diverse cancer types and stages. These images provide the foundation for quantitative feature extraction.

Block 910: Preprocess Image Data (Normalization, Augmentation). Image datasets undergo normalization to standardize pixel intensity and augmentation (e.g., flipping, scaling) to expand dataset variability and prevent overfitting Block 912: Acquire Synthetic Patient Narratives. Unstructured narratives are collected to capture patient-reported experiences, covering emotional, cognitive, and social dimensions.

Block 914: Preprocess Text Data (Cleaning, Tokenization). Narrative data is prepared through text-cleaning processes such as tokenization, lemmatization, and stop-word removal to enable structured thematic analysis.

Model Development and Training

Block 916: Train ResNet-50 Model on Images. A ResNet-50 deep residual network is trained on preprocessed images. Its deep convolutional layers facilitate extraction of intricate diagnostic features.

Block 918: Extract Diagnostic Features from Images. From ResNet-50, high-dimensional diagnostic features are extracted, highlighting cancerous and non-cancerous tissue patterns.

Block 920: Apply Thematic Analysis to Narratives. Thematic analysis is applied to preprocessed narratives, enabling systematic identification of recurring codes and clusters.

Block 922: Identify Themes (Emotional, Cognitive, Social). Themes such as emotional clarity, cognitive insight, support systems, and decision participation are extracted from narrative data to contextualize diagnostics.

Multimodal Integration

Block 924: Fuse ResNet-50 Output with TA Themes. Outputs from the DRL and TA streams are aligned and fused into a unified representation, ensuring both pathological and psychosocial factors are included.

Block 926: Generate Diagnostic Profiles. Integrated diagnostic profiles are generated, combining quantitative predictions with qualitative insights, resulting in a holistic diagnostic view.

Validation and Interpretation

Block 928: Cross-validate Model with Synthetic Data. The integrated framework is cross-validated using synthetic datasets to ensure robustness and generalization.

Block 930: Evaluate Metrics (Accuracy, Precision, Recall, F1). Quantitative performance metrics are calculated to assess diagnostic strength. High scores across accuracy, precision, and recall validate model reliability.

Block 932: Interpret Patient Themes. Narrative-derived themes are interpreted alongside quantitative outputs to contextualize results within patient experiences.

Block 934: Align Clinical Results with Narrative Context. Quantitative outcomes are aligned with patient themes, ensuring interpretability and clinical relevance for personalized care.

Conclusion and Future Directions

Block 936: Summarize Key Findings. Key diagnostic improvements from multimodal integration are synthesized, highlighting reduced false positives and negatives.

Block 938: Highlight Theoretical Contributions. The theoretical contributions of combining DRL and TA are emphasized, particularly the ability to capture both biological and psychosocial dimensions.

Block 940: Propose Clinical Validation Pathways. The framework concludes by outlining potential clinical deployment and validation pathways, enabling translation of research outcomes into real-world oncology practice.

Figure 10:
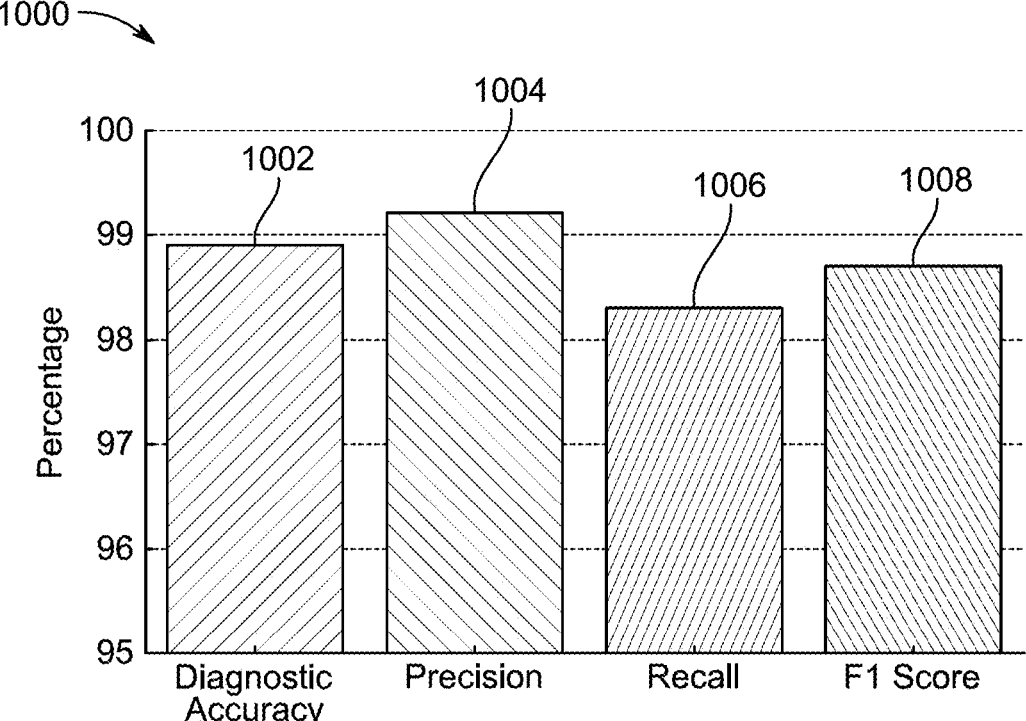
FIG. 10 illustrates a bar chart that represents evaluation metrics of integrated diagnostic framework, according to an embodiment of the present invention.

FIG. 10 illustrates a bar chart 1000 that represents evaluation metrics of integrated diagnostic framework comprising a ResNet-50 based deep residual learning model and thematic analysis. The chart depicts multiple performance metrics that collectively validate the efficacy of the proposed methodology.

1002: The metric of diagnostic accuracy is represented with a value of 98.9%, confirming the capability of the integrated framework to correctly classify cancer-related cases across diverse input data.

1004: Precision is illustrated with a value of 99.2%, indicating the efficiency of the framework in reducing false positives while maintaining correct identification of positive cases.

1006: The recall metric is shown at 98.3%, reflecting the framework's sensitivity in identifying true positive instances and thereby demonstrating its effectiveness in capturing the majority of relevant diagnostic cases.

1008: The F1 score, represented at 98.7%, constitutes a balanced measure between precision and recall, highlighting the overall reliability and effectiveness of the integrated approach.

Collectively, these metrics, as depicted in FIG. 10, substantiate the strength of the framework and establish its practical diagnostic potential within clinical and research-oriented settings.

The integration of Deep Residual Learning (DRL) with Thematic Analysis (TA) has demonstrated significant enhancements in diagnostic accuracy within oncology. By combining quantitative imaging data with qualitative patient narratives, this multimodal approach addresses the complexities of cancer diagnostics in a more comprehensive manner. The ResNet-50 architecture, a prominent DRL model, has been effectively utilized in various cancer detection tasks. In breast cancer diagnostics, the application of ResNet-50 has led to improved accuracy rates by leveraging its deep convolutional layers to extract intricate features from histopathological images. Similarly, in brain tumor detection, the use of ResNet-50 has achieved impressive accuracy and precision rates, underscoring its capability in handling complex imaging data. Beyond imaging, the incorporation of TA provides valuable insights into patient experiences, capturing emotional, cognitive, and social dimensions that are often overlooked in traditional diagnostics. This qualitative analysis enriches the diagnostic process, facilitating more personalized and empathetic patient care. The fusion of DRL and TA within a unified framework enhances the diagnostic process by improving the sensitivity and specificity of cancer detection through advanced image analysis, providing a holistic understanding of patient experiences leading to more tailored treatment plans, and reducing diagnostic errors by integrating multiple data modalities, thereby increasing overall diagnostic confidence.

Figure 11:
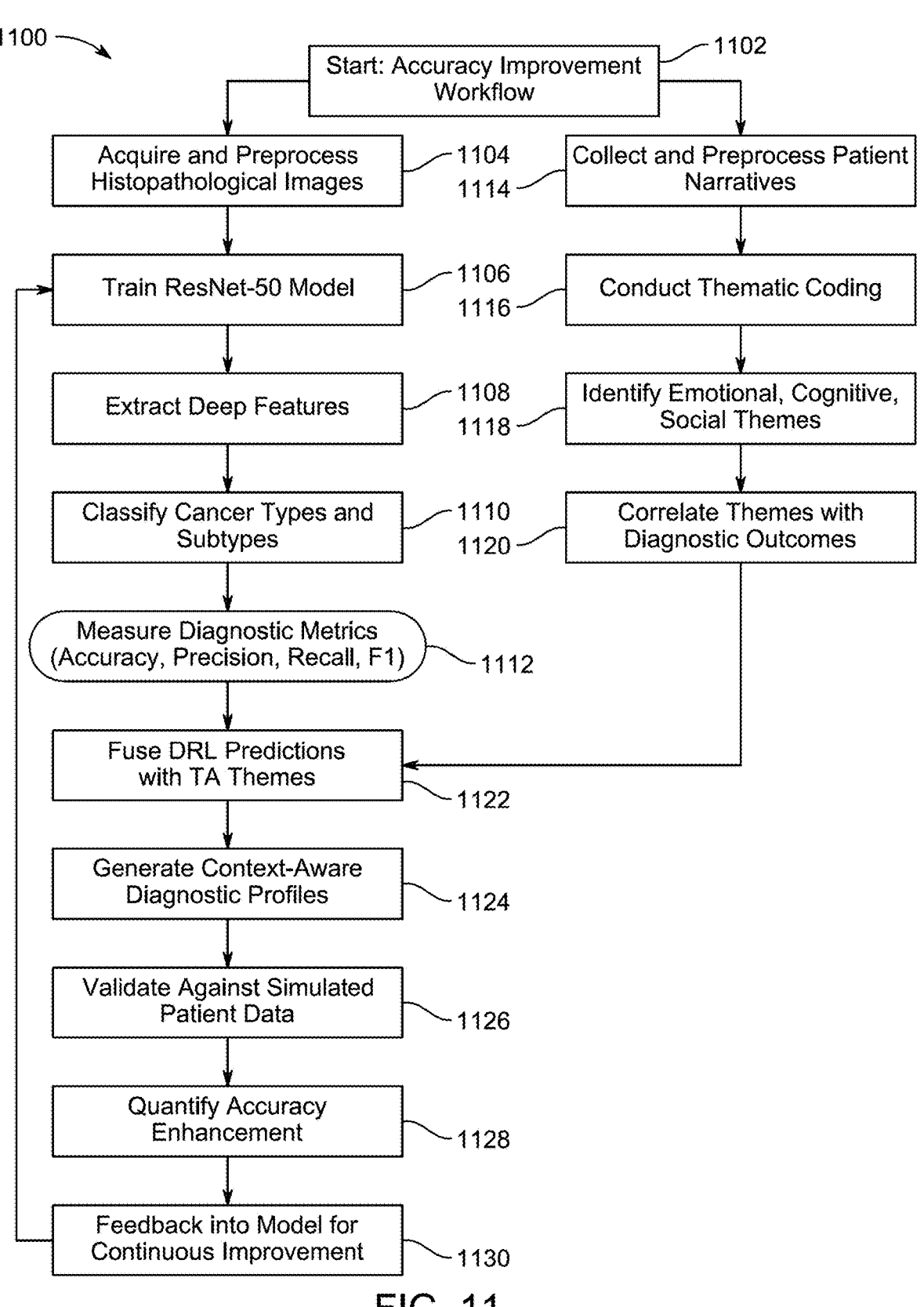
FIG. 11 illustrates a flow diagram that represents diagnostic enhancements through the deep residual learning (DRL) and the thematic analysis (TA), according to an embodiment of the present invention.

FIG. 11 illustrates a flow diagram 1100 that represents diagnostic enhancements through the deep residual learning (DRL) and the thematic analysis (TA). The flowchart demonstrates how structured imaging data and unstructured patient narratives are processed in parallel, then fused to create context-aware diagnostic outputs.

Block 1102: Start: Accuracy Improvement Workflow. The process begins with the initialization of an accuracy improvement pipeline aimed at enhancing diagnostic performance by leveraging multimodal data sources.

Block 1104: Acquire and Preprocess Histopathological Images. Histopathological images are collected from clinical repositories. Preprocessing is performed to normalize image resolution, remove noise, and prepare the dataset for deep learning.

Block 1106: Train ResNet-50 Model. A ResNet-50-based Deep Residual Learning model is trained on the preprocessed images to capture hierarchical representations of histological patterns.

Block 1108: Extract Deep Features. Deep features are extracted from trained convolutional layers to capture morphological and cellular characteristics essential for cancer classification.

Block 1110: Classify Cancer Types and Subtypes. The extracted features are classified into cancer types and subtypes, enabling precise diagnostic predictions grounded in histopathological evidence.

Block 1112: Measure Diagnostic Metrics (Accuracy, Precision, Recall, F1). Diagnostic outcomes are quantitatively assessed using accuracy, precision, recall, and F1-score, establishing baseline model performance.

Block 1114: Collect and Preprocess Patient Narratives. Patient narratives, including interviews, reports, and subjective accounts, are collected. Preprocessing (e.g., text normalization, removal of irrelevant tokens) ensures readiness for analysis.

Block 1116: Conduct Thematic Coding. Narrative data is analyzed through thematic coding to extract key concepts, linguistic markers, and recurring expressions relevant to health outcomes.

Block 1118: Identify Emotional, Cognitive, Social Themes. From coded data, psychosocial themes (e.g., emotional distress, cognitive interpretations, social factors) are identified as qualitative indicators of patient condition.

Block 1120: Correlate Themes with Diagnostic Outcomes. Extracted themes are mapped to diagnostic outcomes, revealing relationships between patient-reported experiences and objective clinical findings.

Block 1122: Fuse DRL Predictions with TA Themes. Outputs from the DRL classifier (steps 1106-1112) are integrated with thematic insights (steps 1114-1120). This fusion creates enriched diagnostic predictions that combine clinical precision with contextual understanding.

Block 1124: Generate Context-Aware Diagnostic Profiles. Multimodal integration results in diagnostic profiles that are sensitive to both pathological image features and psychosocial patient context, improving personalization and interpretability.

Block 1126: Validate Against Simulated Patient Data. Context-aware profiles are validated using simulated patient datasets to evaluate robustness and generalizability.

Block 1128: Quantify Accuracy Enhancement. Improvements in performance metrics (false positives, false negatives, overall accuracy) are quantified, demonstrating the advantage of the integrated approach.

Block 1130: Feedback into Model for Continuous Improvement. A feedback loop reintroduces validated outcomes and quantified improvements into the DRL-TA framework, enabling iterative refinement and sustained accuracy gains over time.

Figure 12:
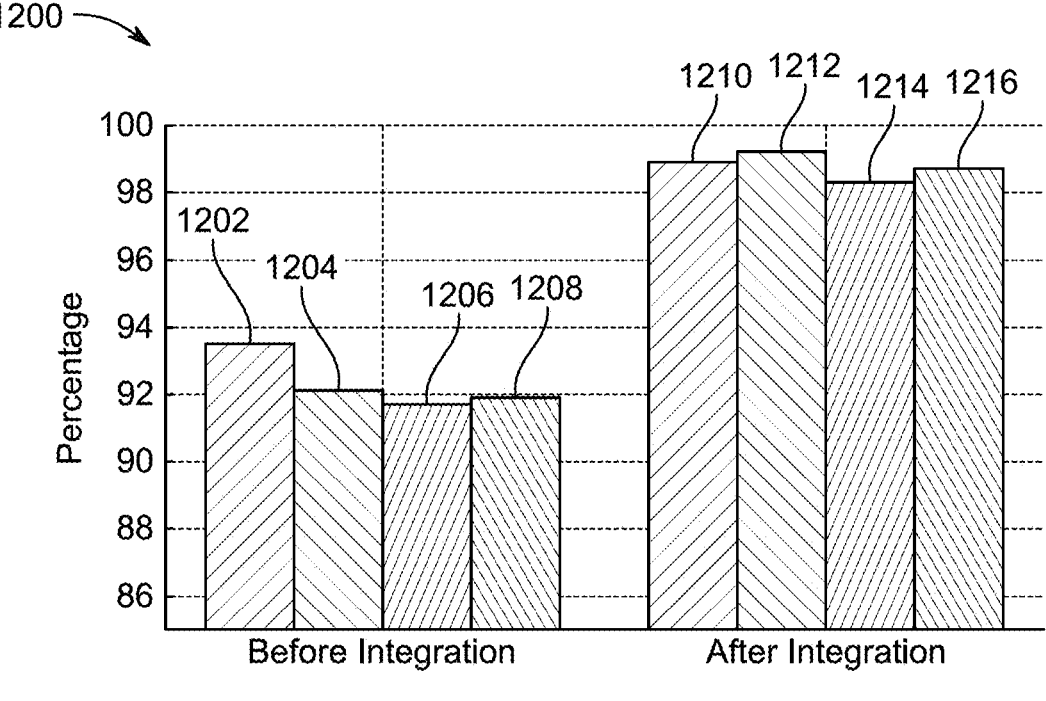
FIG. 12 illustrates a grouped bar chart that provides a comparative analysis of diagnostic performance metrics before and after the integration of deep residual learning (DRL) with thematic analysis (TA), according to an embodiment of the present invention.

FIG. 12 illustrates a grouped bar chart 1200 that provides a comparative analysis of diagnostic performance metrics before and after the integration of deep residual learning (DRL) with thematic analysis (TA). The grouped representation highlights four key metrics: accuracy, precision, recall, and F1 score. Each metric is depicted in two bars, corresponding to the performance of the standalone DRL model (before integration) and the integrated DRL+TA framework (after integration).

The "before integration" results represent the diagnostic performance achieved solely through the ResNet-50 based DRL model. These values 1202, 1204, 1206, 1208 reflect the strength of quantitative imaging analysis in detecting cancer cases, but remain limited in capturing patient-centered dimensions of the diagnostic process. By contrast, the "after integration" results capture the improvements attained when patient narratives, analyzed through thematic analysis, are incorporated alongside imaging-based quantitative features.

As shown in the grouped bar chart, significant enhancements are observed across all four performance measures 1210, 1212, 1214, 1216. Accuracy demonstrates an overall uplift, confirming the higher correctness of classification outcomes. Precision exhibits a notable improvement, reflecting the model's enhanced ability to minimize false positives by leveraging thematic insights. Recall also records substantial gains, showing improved sensitivity in identifying true positives and thereby reducing false negatives. The F1 score (performance measure 1216), representing the harmonic mean of precision and recall, rises accordingly, affirming the overall balanced performance of the integrated methodology.

The comparative visualization in FIG. 12 substantiates the practical advantage of multimodal fusion. By combining DRL-driven image analysis with TA-derived contextual insights, the integrated framework demonstrates improved diagnostic reliability and contextual sensitivity, aligning with the goals of precision medicine. This confirms that the fusion of imaging features with patient-reported themes not only strengthens classification accuracy but also enriches the interpretability of diagnostic outcomes, ultimately supporting more personalized and empathetic cancer care.

Figure 13A:
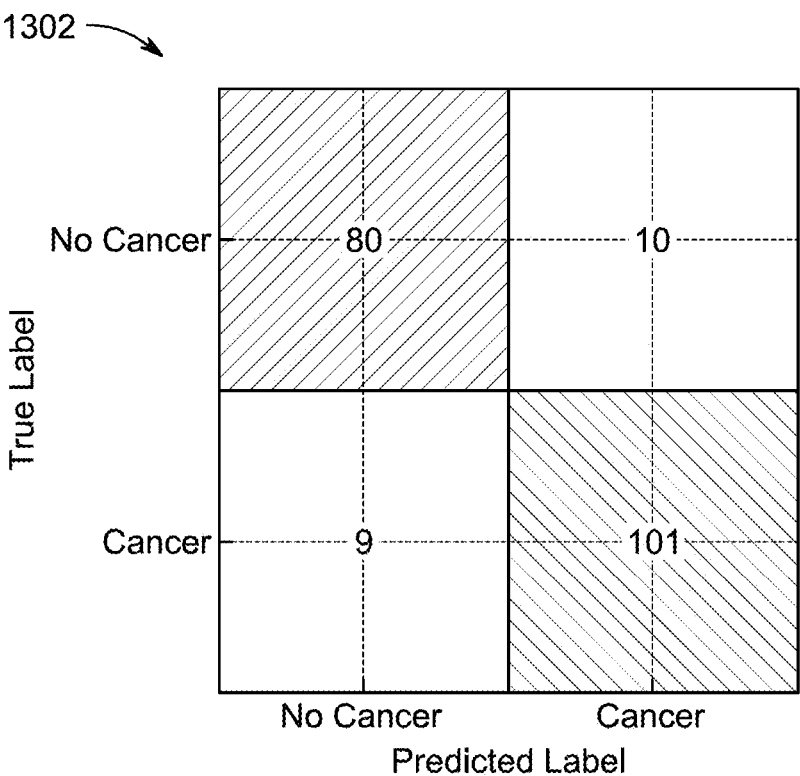
FIG. 13A depicts a representation illustrating the error profile of the standalone DRL model, according to an embodiment of the present invention.
Figure 13B:
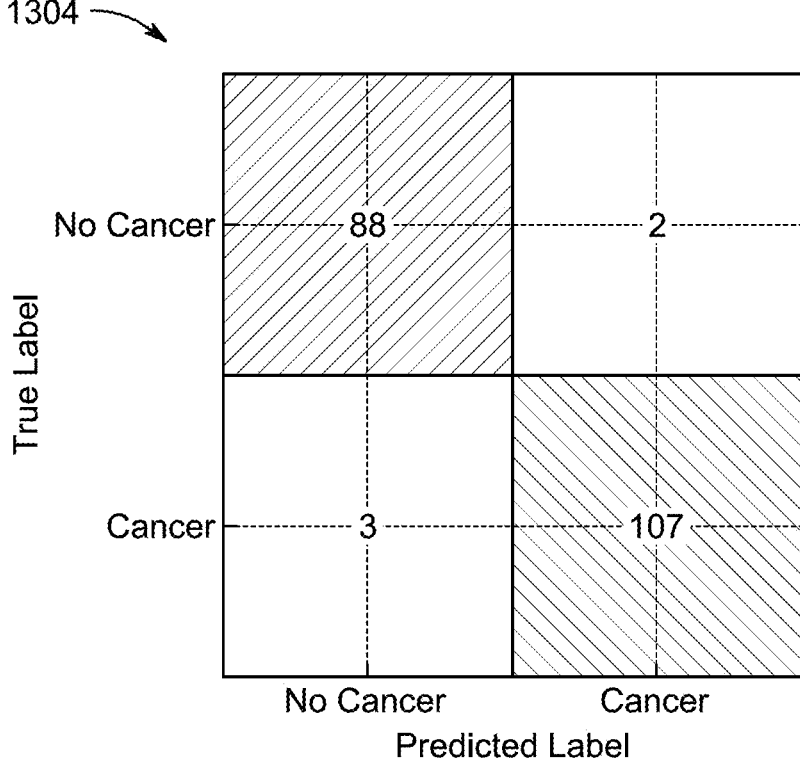
FIG. 13B depicts a representation illustrating the results after incorporating thematic analysis into the diagnostic pipeline, according to an embodiment of the present invention.

FIG. 13A and FIG. 13B collectively illustrate the comparative error distribution in diagnostic predictions before and after the integration of deep residual learning (DRL) with thematic analysis (TA).

FIG. 13A depicts a representation 1302 illustrating the error profile of the standalone DRL model. Although the ResNet-50 based architecture exhibits strong classification capability, it still produces notable error counts. Specifically, the model records ten false positives, where non-cancerous cases are incorrectly classified as cancerous, and nine false negatives, where cancerous cases are missed. These errors reflect the limitations of relying solely on imaging features, particularly in ambiguous or borderline diagnostic scenarios.

FIG. 13B depicts a representation 1304 illustrating the results after incorporating thematic analysis into the diagnostic pipeline. By integrating patient narratives with imaging-derived features, the framework achieves a marked reduction in diagnostic errors. False positives are reduced from ten to two, and false negatives are reduced from nine to three. This sharp decline confirms that contextual insights extracted from patient-reported experiences enhance the discriminative capacity of the overall system.

The comparison between FIG. 13A and FIG. 13B underscores the diagnostic benefit of merging structured quantitative data with qualitative thematic insights. These improvements highlight the potential of the proposed multimodal framework to deliver more reliable, interpretable, and patient-centered cancer diagnostics.

Figure 14:
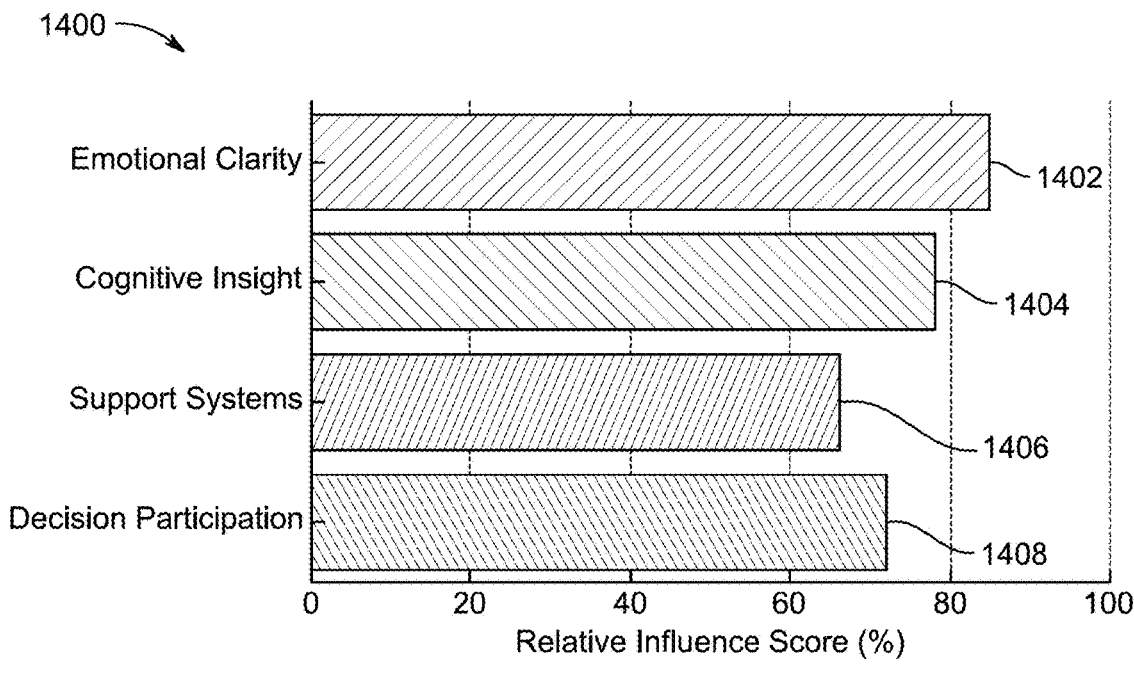
FIG. 14 illustrates a bar chart that represents thematic dimensions influencing diagnostic contextualization, according to an embodiment of the present invention.

FIG. 14 illustrates a bar chart 1400 that represents thematic dimensions influencing diagnostic contextualization. The Y-axis represents key thematic dimensions, including emotional clarity, cognitive insight, support systems, and decision participation. The X-axis denotes the relative influence score expressed as a percentage ranging from 0 to 100.

The results demonstrate that Emotional Clarity 1402 exhibits the highest influence score at approximately 85%. This indicates that the ability of patients to articulate and process their emotions significantly enhances the interpretive context of diagnostic outcomes. Cognitive Insight 1404 yields a score of 78%, underscoring the role of patient understanding and meaning-making processes in enhancing diagnostic interpretation.

Support systems 1406 register a relative influence of approximately 66%, underscoring the importance of social and relational factors in shaping patient well-being and diagnostic outcomes. Decision participation 1408 achieves a score of approximately 72%. This dimension emphasizes the role of patient involvement in shared decision-making, reflecting its value in aligning diagnostic assessments with patient preferences and expectations.

The findings represented in FIG. 14 validate the contribution of thematic analysis beyond quantitative accuracy. By integrating thematic dimensions into the diagnostic process, the system 100 introduces interpretive empathy, enriching diagnostic reliability while aligning clinical insights with patients lived realities. This embodiment demonstrates that thematic analysis not only augments the technical accuracy of the model but also enables personalization and human-centered care in oncology diagnostics.

A further embodiment relates to a comparative performance evaluation of the proposed framework. The integration of Deep Residual Learning (DRL) with Thematic Analysis (TA) has been systematically evaluated against traditional diagnostic models to assess measurable improvements in accuracy, precision, recall, and overall reliability. This comparative analysis demonstrates the superiority of the integrated DRL+TA framework relative to standalone DRL models and other conventional diagnostic approaches.

Figure 15:
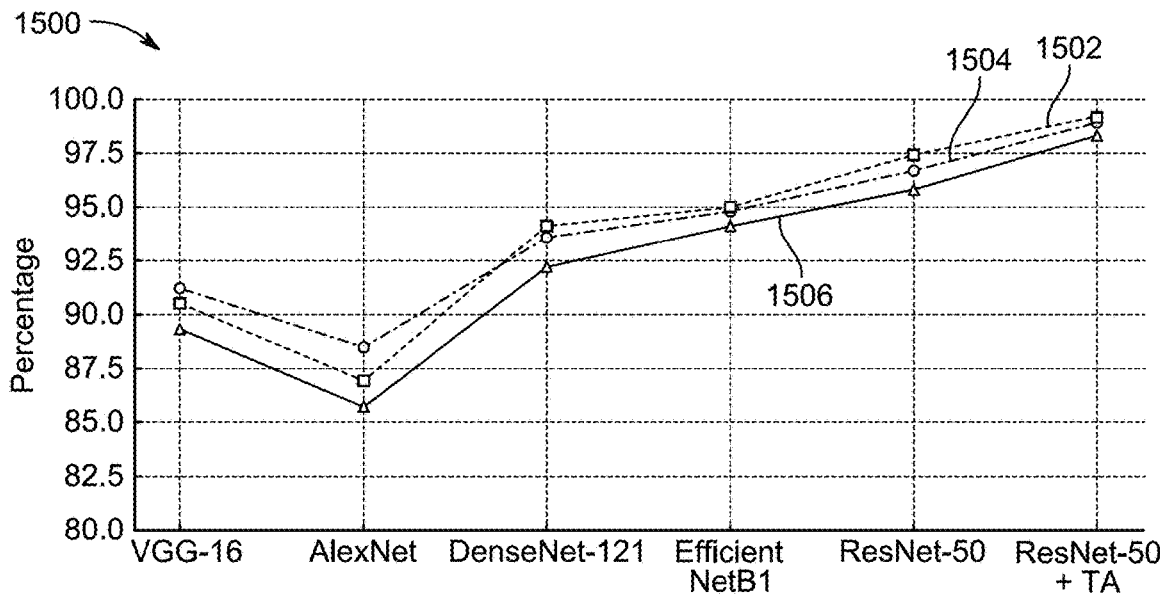
FIG. 15 illustrates a graphical representation of comparative performance of diagnostic models, according to an embodiment of the present invention.

FIG. 15 illustrates a graphical representation 1500 of comparative performance of diagnostic models based on three performance metrics, namely accuracy, precision, and recall. The x-axis of the figure represents different model architectures, including VGG, AlexNet, DenseNet, EfficientNetB1, ResNet-50, and ResNet-50 combined with Thematic Analysis (TA). The y-axis represents the percentage scale ranging from 80% to 100%.

The graph plots three key performance metrics for each model:

Metric 1502 represents Accuracy, metric 1504 represents precision, and metric 1506 represents recall.

Traditional models, such as AlexNet and VGG-16, exhibit relatively lower and inconsistent performance across all three metrics. Their metrics for accuracy, precision, and recall are all below 92.5%, and the performance of AlexNet, in particular, drops to approximately 88.5% for accuracy, 87% for precision, and just above 85% for recall. This highlights the limitations of these older, simpler architectures in comparison to more modern models. There is a significant jump in performance with DenseNet-121 and subsequent models. DenseNet-121 achieves accuracy and precision of around 94% and recall of about 92.5%. EfficientNetB1 and ResNet-50 continue this trend of improvement. ResNet-50, as noted, achieves a precision of 97.4% and an accuracy of 96.7%. The consistent upward slope of all three lines demonstrates that these newer, deeper, and more complex architectures are more effective at the diagnostic task.

The most crucial finding of the graph is the performance of the ResNet-50+TA (Thematic Analysis) configuration. This model represents the peak performance, with all three metrics clustered near the 99% mark.

Precision is the highest at 99.2%.

Accuracy is at 98.9%.

Recall is approximately 98.0%.

This data visually reinforces the hypothesis that combining quantitative image analysis (via ResNet-50) with qualitative insights (Thematic Analysis) leads to a synergistic effect, enhancing the model's ability to correctly classify, with higher precision and overall accuracy. The high precision and recall values suggest that the model is both highly effective at identifying true positive cases (precision) and at finding all relevant cases (recall), making it a robust tool for diagnostic purposes.

The comparative results presented in FIG. 15 reinforce the technical conclusion that multimodal fusion enhances diagnostic robustness and sensitivity. By integrating thematic context with image-based classification, the proposed framework significantly reduces both false positives and false negatives, thereby advancing the state of cancer diagnostics toward greater accuracy, interpretability, and patient-centered care.

Figure 16:
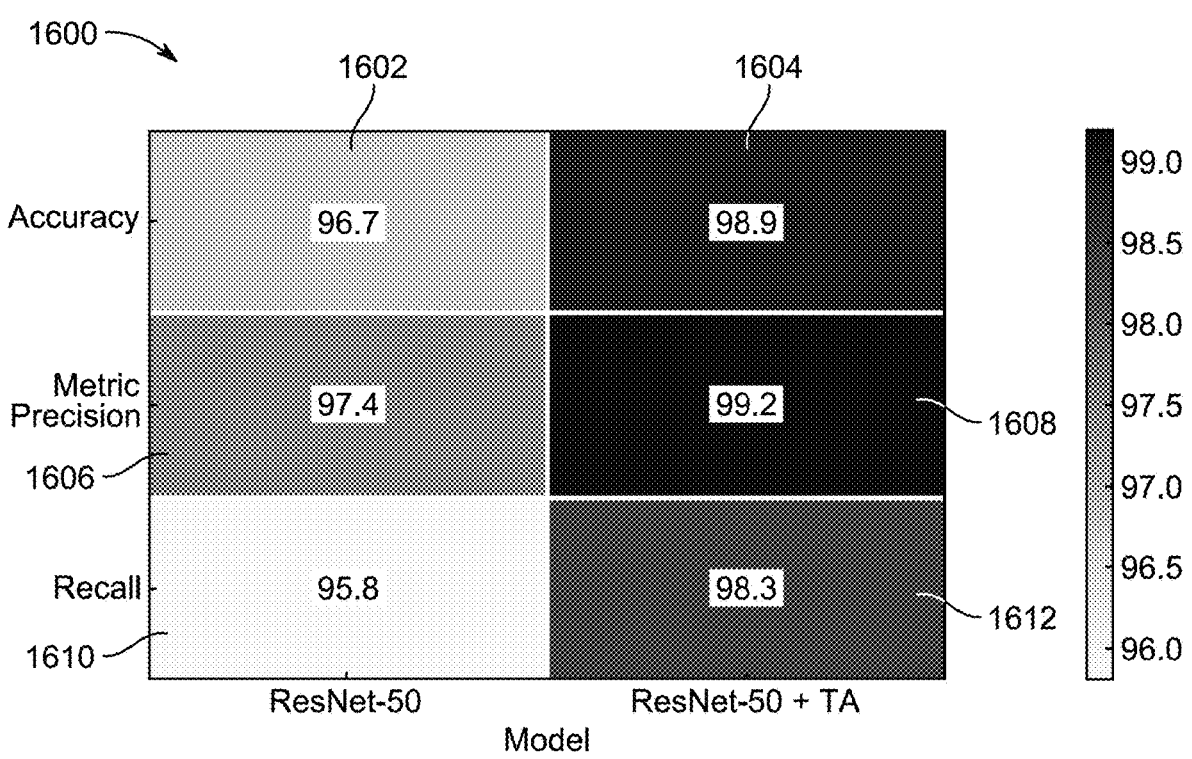
FIG. 16 represents a heatmap depicting "Metric Comparison-ResNet-50 vs ResNet-50+Thematic Analysis", according to an embodiment of the present invention.

FIG. 16 represents a heatmap 1600 depicting "Metric Comparison-ResNet-50 vs ResNet-50+Thematic Analysis." The figure is designed to visually compare the performance of two models: ResNet-50 and ResNet-50+TA (Thematic Analysis). The y-axis lists the performance metrics: Accuracy, Precision, and Recall. The x-axis displays the two models being compared: ResNet-50 and ResNet-50+TA.

The heatmap represents the percentage values. 1602, 1606, 1610 correspond to lower percentages (around 95.8%), while 1604, 1608, 1612 represent higher percentages (up to 99.2%). Each cell within the heatmap contains the specific percentage value for each metric-model combination, allowing for a precise numerical comparison in addition to the visual one.

The figure shows consistent improvement across all three metrics after the integration of Thematic Analysis (TA):

Accuracy: The model's overall correctness, Accuracy, increases from 96.7% (ResNet-50) to 98.9% (ResNet-50+TA).

Precision: The ability to correctly identify positive cases, Precision, shows the largest jump, rising from 97.4% to 99.2%. This indicates a substantial reduction in false positives.

Recall: The ability to find all positive cases, Recall, also improves significantly, from 95.8% to 98.3%. This indicates fewer false negatives.

The heatmap visually and numerically affirms that a multimodal approach, combining quantitative image analysis (ResNet-50) with qualitative insights (Thematic Analysis), enhances diagnostic abilities. The improved metrics, especially the high precision and recall, signify enhanced diagnostic clarity, reduced misclassification rates, and improved sensitivity to the specific patterns (e.g., cancerous patterns) the model is trained to detect.

Figure 17:
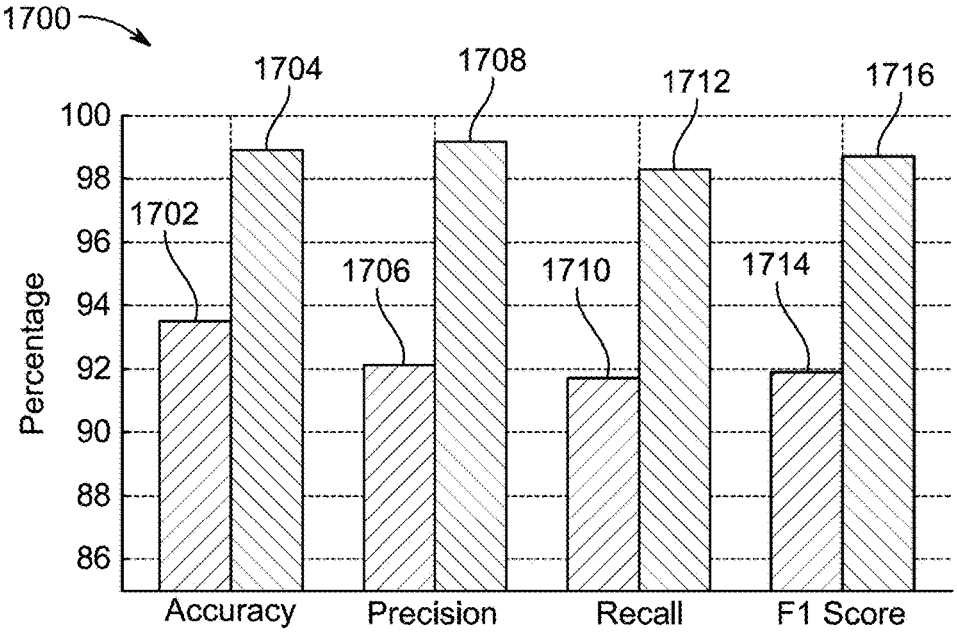
FIG. 17 is a graphical representation illustrating "Performance of ResNet-50 vs. ResNet-50+Thematic Analysis", according to an embodiment of the present invention.

FIG. 17 is a graphical representation 1700 illustrating "Performance of ResNet-50 vs. ResNet-50+Thematic Analysis." The graphical representation 1700 is designed to compare the performance of a standard ResNet-50 model with a modified version that includes Thematic Analysis (TA). The x-axis lists four performance metrics: Accuracy, Precision, Recall, and F1 Score. The y-axis represents the percentage score for each metric, ranging from 0% to 100%.

For each metric, there are two distinct bars:

Bars 1702, 1706, 1710, 1714 on the left represent the performance of the ResNet-50 model (before integration).

Bars 1704, 1708, 1712, 1716 on the right represent the performance of the ResNet-50+TA model (after integration).

The height of each bar corresponds to its respective percentage score, with the exact values displayed on top of each bar for easy comparison. Bars 1702, 1706, 1710, 1714 are consistently taller than the Bars 1704, 1708, 1712, 1716, visually representing the improvement across all metrics.

Accuracy: The overall correctness of the model's predictions, Accuracy, increases from 93.5% for ResNet-50 to 98.9% for ResNet-50+TA. This reflects a significant gain in the model's overall reliability.

Precision and Recall: These two metrics, which are crucial for diagnostics, both show substantial gains of over 6%. Precision, which measures the proportion of true positive predictions among all positive predictions, and Recall, which measures the proportion of true positives identified out of all actual positives, both improve significantly. This indicates a reduction in both false positives and false negatives, leading to fewer diagnostic errors and increased confidence in the model's output.

F1 Score: The F1 Score is the harmonic mean of precision and recall. It provides a single metric that balances both values, making it particularly useful for models where both false positives and false negatives are important to minimize. The F1 Score for the combined model jumps from 91.9% to 98.7%, a gain of nearly 7%, indicating the overall balanced performance of the model in correctly identifying cases while avoiding misclassifications.

Figure 18:
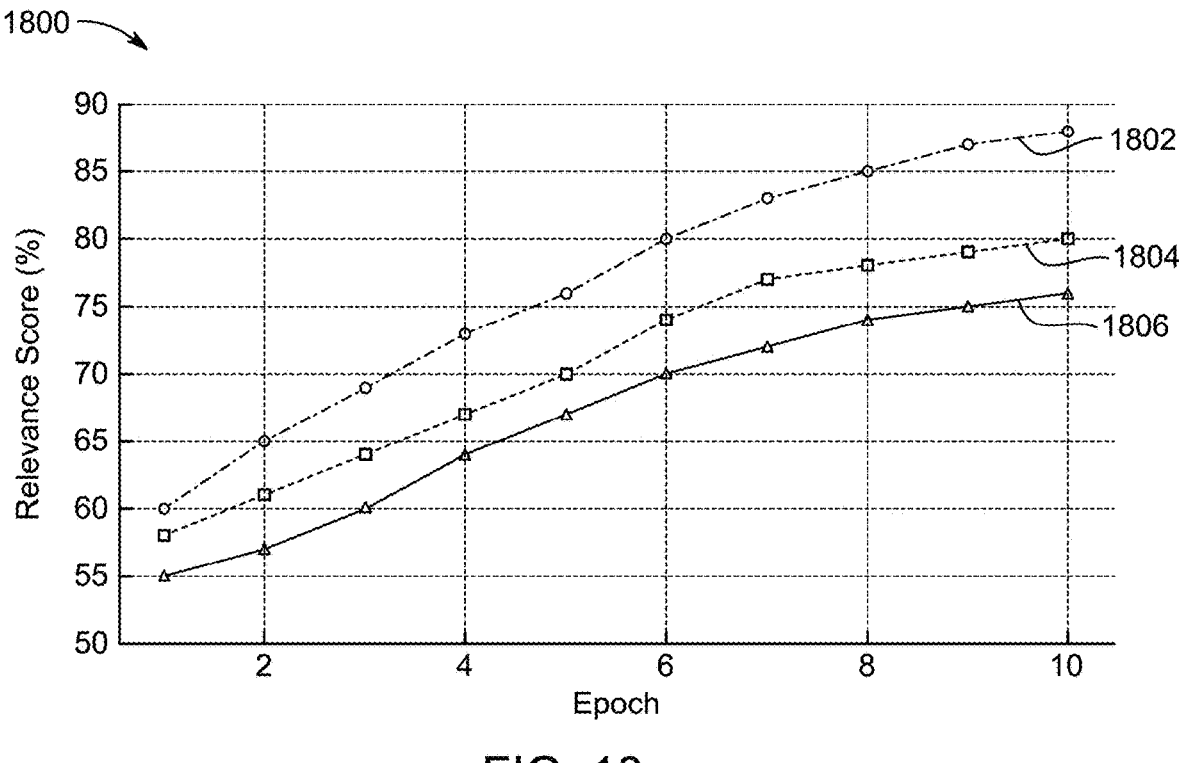
FIG. 18 is a graphical representation depicting thematic signal contribution across simulation epochs, according to an embodiment of the present invention.

FIG. 18 is a graphical representation 1800 depicting thematic signal contribution across simulation epochs, which shows the progressive influence of three different thematic dimensions on a diagnostic model over time. The x-axis represents Epoch, which likely refers to a training or simulation step, ranging from 1 to 10. The y-axis represents the Relevance Score (%), ranging from 50% to 90%, indicating how much each theme contributes to the model's diagnostic process.

The graph plots three distinct lines, each representing a thematic dimension:

A line 1802 with circles represents Emotional Themes.

A line 1804 with squares represents Cognitive Themes.

A line 1806 with triangles represents Social Themes.

All three lines show a consistent upward trend, indicating that the relevance of each thematic signal increases over the simulation epochs. Line 1802 (Emotional Themes) starts at a higher relevance score and maintains the steepest growth rate. Lines 1804 and 1806 (Cognitive and Social Themes) also rise but at a more gradual pace. The progressive strengthening of all three thematic signals confirms their growing role in refining diagnostics. By learning to incorporate these human-centric data points, the model can move beyond simple pattern recognition to deliver more empathetic and personalized diagnostic outputs, which is a key advantage of the multimodal approach.

In one exemplary embodiment, multiple deep learning architectures may be deployed for the classification of pathological conditions using medical imaging data. Comparative testing of such architectures demonstrates that residual network models consistently provide superior accuracy and precision, thereby establishing a baseline for their suitability in complex diagnostic imaging applications.

In another embodiment, convolutional neural network (CNN) based approaches may be evaluated for the classification of segmented lesion images. Residual network models have demonstrated enhanced recall in identifying subtle pathological variations, particularly in early-stage malignancies, which may not be effectively captured by shallower network configurations.

In further embodiments, adjusted or fine-tuned residual network configurations may achieve precision values exceeding 95% and area under the curve (AUC) values approaching 0.97 across diverse cancer prediction tasks. These outcomes surpass those observed with alternative deep learning models, underscoring the robustness of residual learning approaches in clinical diagnostics.

These comparative evaluations highlight the diagnostic advantages of the integrated Deep Residual Learning (DRL) and the Thematic Analysis (TA) framework. The fusion of quantitative imaging insights obtained from DRL with qualitative thematic insights derived from patient narratives enables a holistic and clinically robust diagnostic process. The inclusion of TA enriches the interpretability of model outputs, reduces diagnostic uncertainty, and enhances alignment with patient-specific contexts. Collectively, these aspects underscore the technical novelty of the integrated methodology, demonstrating its potential for adoption in precision oncology workflows.

The integration of the DRL with the TA in cancer diagnostics represents a substantial advancement in the field, wherein quantitative imaging data is combined with qualitative patient narratives to enhance diagnostic accuracy and promote patient-centered care. The use of DRL models, particularly the ResNet-50 architecture, has demonstrated exceptional performance across multiple cancer detection tasks. For example, in breast cancer diagnostics, ResNet-50 achieved an accuracy of 96 percent and an F1 score of 94.66 percent on the CBIS-DDSM dataset, outperforming traditional architectures such as VGG16 and VGG19. Similarly, in brain tumor detection, ResNet-50 attained an accuracy of 92 percent and a precision of 94 percent, thereby underscoring its effectiveness in handling complex imaging data. In lung cancer prediction, an adjusted ResNet-50 model achieved a precision of 98.1 percent and an AUC value of 0.97, surpassing other models such as EfficientNetB1 and Inception V3.

The incorporation of TA within the framework provides an additional dimension of analysis by capturing emotional, cognitive, and social aspects of patient experiences.

The fusion of DRL and TA in a unified framework thus enhances the diagnostic process by:

improving sensitivity and specificity through advanced image-based analysis, providing a holistic view of patient experiences, and reducing diagnostic errors by integrating multiple data modalities.

This integrated methodology aligns with the paradigm of precision medicine, where the convergence of advanced computational techniques and patient-centered approaches is recognized as paramount to improving clinical outcomes.

Interpretation of Simulation Outcomes

The simulation outcomes of the integrated Deep Residual Learning (DRL) and Thematic Analysis (TA) framework further underscore its efficacy as an advanced diagnostic tool. By merging quantitative imaging data with qualitative patient narratives, the framework produces a more comprehensive diagnostic representation of patient health, resulting in enhanced accuracy and the ability to support more individualized treatment planning.

The DRL component, particularly leveraging architectures such as ResNet-50, demonstrates strong proficiency in analyzing complex histopathological images, aligning with broader findings in oncology research that establish the role of deep learning in enabling precise cancer diagnosis and prognosis through large-scale data integration.

Complementing this quantitative capacity, the TA component contributes valuable insights into patient emotional, cognitive, and social experiences. This dimension enriches diagnostic interpretation by highlighting aspects of well-being and lived experience that are not reflected in imaging data alone.

The fusion of DRL and TA within the simulation framework yields a synergistic effect by enhancing the detection of subtle patterns and correlations that might otherwise be overlooked in unimodal analysis. This multimodal methodology aligns with the principles of precision medicine, enhancing both diagnostic reliability and patient-centered care.

In conclusion, the simulation outcomes validate the technical effectiveness of combining DRL and TA in cancer diagnostics. The proposed framework not only improves diagnostic accuracy but also ensures that patient perspectives and experiences are integrated into the diagnostic and treatment process, thereby contributing to the realization of personalized and effective healthcare solutions.

Although techniques using, and systems including, system and method for generating multimodal diagnostic output have been described in language specific to features and/or methods, it is to be understood that the subject of the appended claims is not necessarily limited to the specific features or methods described. Rather, the specific features and methods are disclosed as example implementations of generating multimodal diagnostic output.

Some embodiments disclose multi-source, real-world datasets, including histopathological slides, radiology scans, genomic profiles, and patient-reported narratives. The embodiments include a simulation-to-clinic pipeline adaptable to authentic hospital data and diverse cancer types.

Some embodiments also disclose a dual-channel modular architecture, separating imaging and narrative streams, each processed by domain-specific encoders and include a context-enriched fusion layer with adaptive weighting and attention mechanisms that dynamically adjust importance of modalities depending on diagnostic ambiguity.

Some embodiments further disclose a thematic signal encoding pipeline for clinical use in a system that standardizes themes (emotional, cognitive, social) into quantitative feature vectors for direct algorithmic use, introducing alignment mechanisms (time stamps, patient IDs) for synchronization with imaging and structured clinical data.

Some embodiments go beyond static fusion by defining a closed-loop system where thematic and imaging weights are iteratively updated based on diagnostic outcomes. These includes a feedback loop to continuously refine decision rules based on patient responses and treatment progress.

Some embodiments further disclose a scalable, modular system (Docker/Kubernetes microservices) with EHR integration (FHIR/HL7), PACS plug-ins, telemedicine APIs, and HIPAA/FDA compliance features, providing explicit commercialization strategies including diagnostic software suites, mobile companion apps, and APIs for health tech partners.

Next, further details of the hardware description of the computing environment of FIG. 1 according to exemplary embodiments are described with reference to FIG. 19.

The hardware elements in order to achieve the computing device may be realized by various circuitry elements, known to those skilled in the art. For example, CPU 1901 or CPU 1903 may be a Xenon or Core processor from Intel of America or an Opteron processor from AMD of America, or may be other processor types that would be recognized by one of ordinary skill in the art. Alternatively, the CPU 1901, 1903 may be implemented on an FPGA, ASIC, PLD or using discrete logic circuits, as one of ordinary skilled in the art would recognize. Further, C P U 1901, 1903 may be implemented as multiple processors cooperatively working in parallel to perform the instructions of the inventive processes described above.

Figure 19:
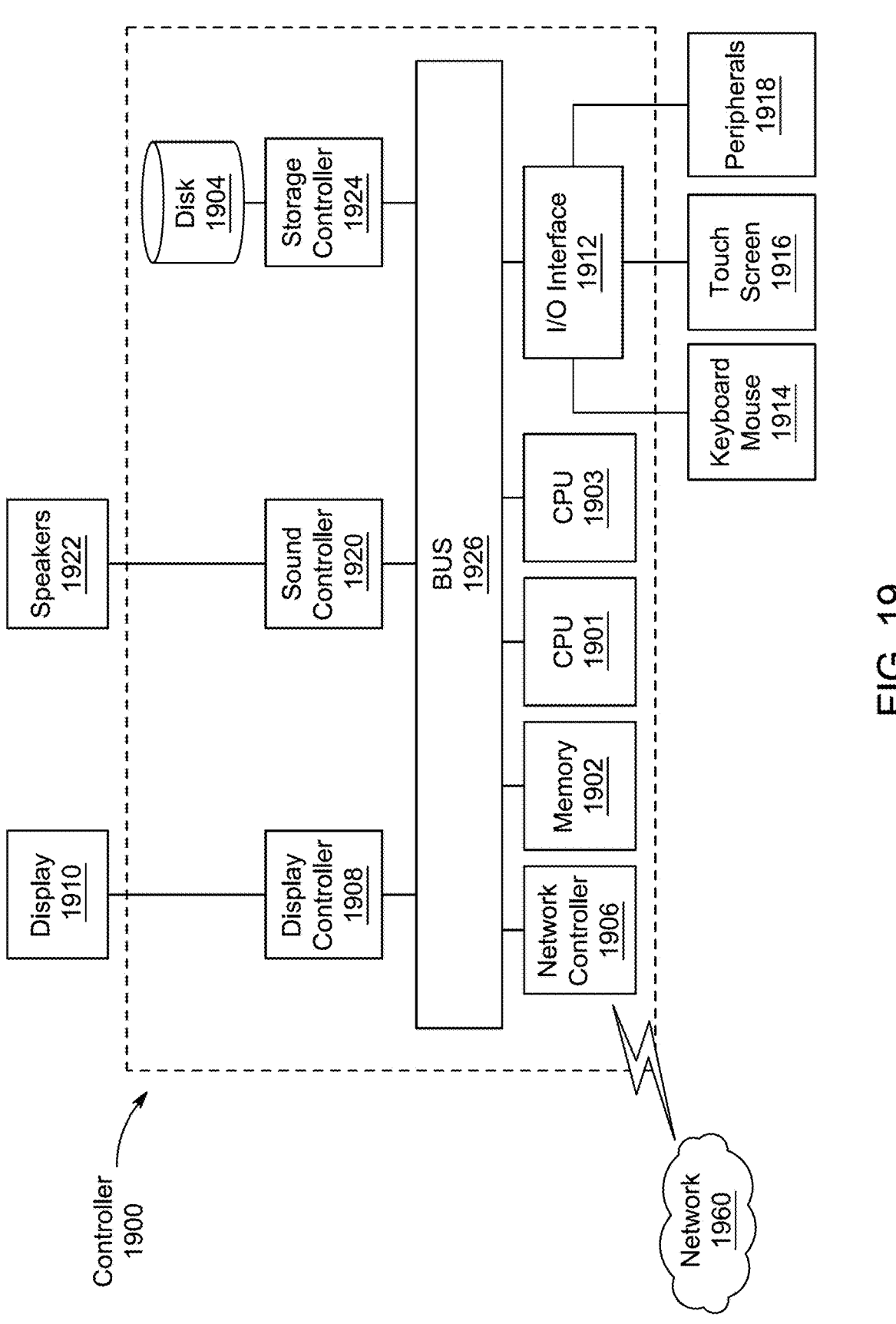
FIG. 19 is an illustration of a non-limiting example of details of computing hardware used in a computing system, according to certain embodiments.

The computing device in FIG. 19 also includes a network controller 1906, such as an Intel Ethernet PRO network interface card from Intel Corporation of America, for interfacing with network 1960. As can be appreciated, the network 1960 can be a public network, such as the Internet, or a private network such as an LAN or WAN network, or any combination thereof and can also include PSTN or ISDN sub-networks. The network 1960 can also be wired, such as an Ethernet network, or can be wireless such as a cellular network including EDGE, 3G and 4G wireless cellular systems. The wireless network can also be WiFi, Bluetooth, or any other wireless form of communication that is known.

The computing device further includes a display controller 1908, such as a NVIDIA Geforce GTX or Quadro graphics adaptor from NVIDIA Corporation of America for interfacing with display 1910, such as a Hewlett Packard HPL2445w LCD monitor. A general purpose I/O interface 1912 interfaces with a keyboard and/or mouse 1914 as well as a touch screen panel 1916 on or separate from display 1910. General purpose I/O interface also connects to a variety of peripherals 1918 including printers and scanners, such as an OfficeJet or DeskJet from Hewlett Packard.

A sound controller 1920 is also provided in the computing device such as Sound Blaster X-Fi Titanium from Creative, to interface with speakers/microphone 1922 thereby providing sounds and/or music.

The general-purpose storage controller 1924 connects the storage medium disk 1904 with communication bus 1926, which may be an ISA, EISA, VESA, PCI, or similar, for interconnecting all of the components of the computing device. A description of the general features and functionality of the display 1910, keyboard and/or mouse 1914, as well as the display controller 1908, storage controller 1924, network controller 1906, sound controller 1920, and general purpose I/O interface 1912 is omitted herein for brevity as these features are known.

The exemplary circuit elements described in the context of the present disclosure may be replaced with other elements and structured differently than the examples provided herein. Moreover, circuitry configured to perform features described herein may be implemented in multiple circuit units (e.g., chips), or the features may be combined in circuitry on a single chipset, as shown on FIG. 19.

Figure 20:
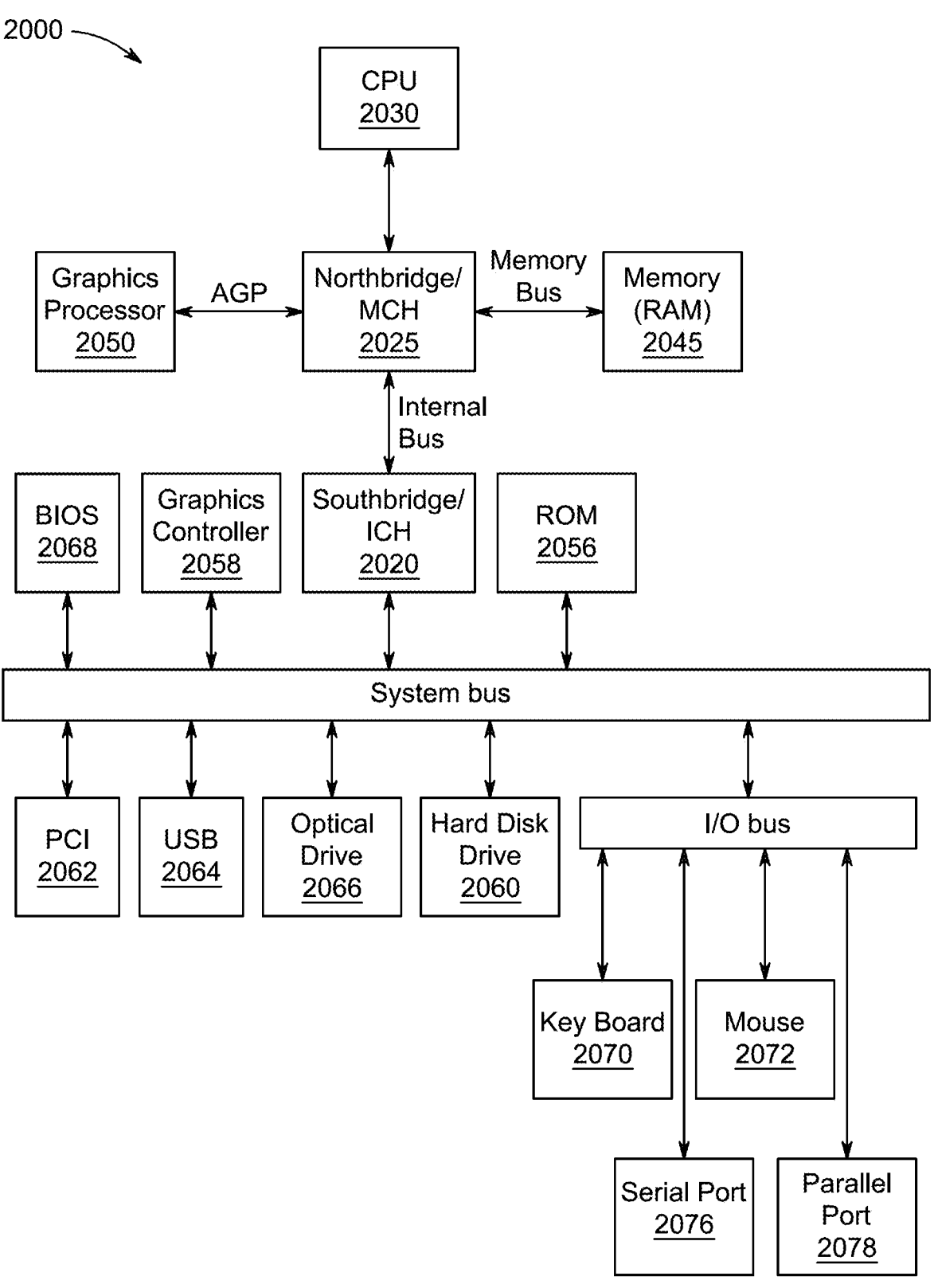
FIG. 20 is an exemplary schematic diagram of a data processing system used within the computing system, according to certain embodiments.

FIG. 20 shows a schematic diagram of a data processing system, according to certain embodiments, for performing the functions of the exemplary embodiments. The data processing system is an example of a computer in which code or instructions implementing the processes of the illustrative embodiments may be located.

In FIG. 20, data processing system 2000 employs a hub architecture including a north bridge and memory controller hub (NB/MCH) 2025 and a south bridge and input/output (I/O) controller hub (SB/ICH) 2020. The central processing unit (CPU) 2030 is connected to NB/MCH 2025. The NB/MCH 2025 also connects to the memory 2045 via a memory bus and connects to the graphics processor 2050 via an accelerated graphics port (AGP). The NB/MCH 2085 also connects to the SB/ICH 2020 via an internal bus (e.g., a unified media interface or a direct media interface). The central processing unit (CPU) 2030 may contain one or more processors and even may be implemented using one or more heterogeneous processor systems.

Figure 21:
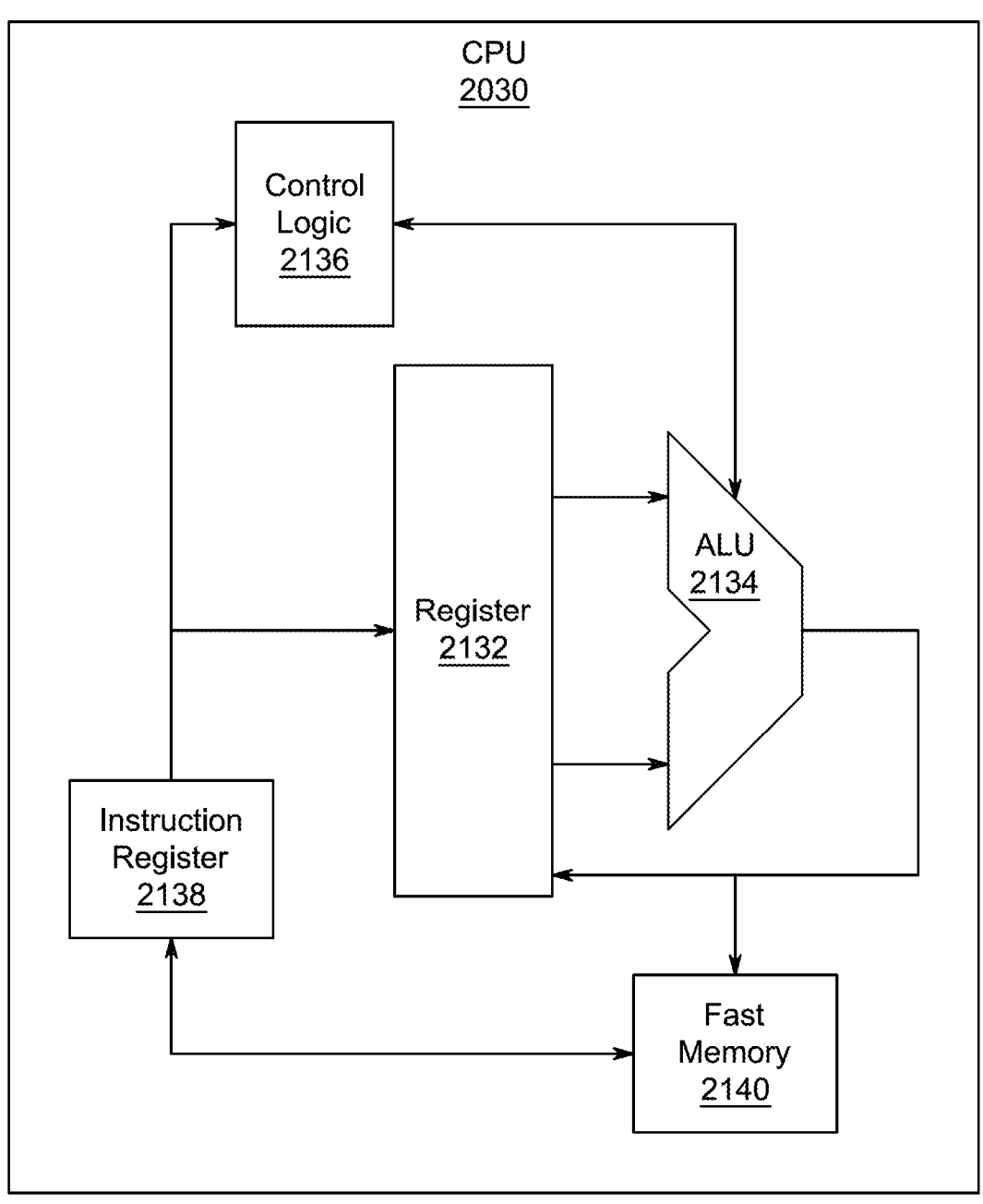
FIG. 21 is an exemplary schematic diagram of a processor used with the computing system, according to certain embodiments.

For example, FIG. 21 shows one implementation of CPU 2030. In one implementation, the instruction register 2138 retrieves instructions from the fast memory 2140. At least part of these instructions is fetched from the instruction register 2138 by the control logic 2136 and interpreted according to the instruction set architecture of the CPU 2130. Part of the instructions can also be directed to the register 2182. In one implementation the instructions are decoded according to a hardwired method, and in another implementation the instructions are decoded according to a microprogram that translates instructions into sets of CPU configuration signals that are applied sequentially over multiple clock pulses. After fetching and decoding the instructions, the instructions are executed using the arithmetic logic unit (ALU) 2134 that loads values from the register 2132 and performs logical and mathematical operations on the loaded values according to the instructions. The results from these operations can be feedback into the register and/or stored in the fast memory 2140. According to certain implementations, the instruction set architecture of the CPU 2030 can use a reduced instruction set architecture, a complex instruction set architecture, a vector processor architecture, and a very large instruction word architecture. Furthermore, the CPU 2030 can be based on the Von Neuman model or the Harvard model. The CPU 2030 can be a digital signal processor, an FPGA, an ASIC, a PLA, a PLD, or a CPLD. Further, the CPU 2030 can be an x56 processor by Intel or by AMD, an ARM processor, a Power architecture processor by, e.g., IBM; a SPARC architecture processor by Sun Microsystems or by Oracle; or other known CPU architecture.

Referring again to FIG. 20, the data processing system 2000 can include that the SB/ICH 2080 is coupled through a system bus to an I/O Bus, a read only memory (ROM) 2056, universal serial bus (USB) port 2064, a flash binary input/output system (BIOS) 2068, and a graphics controller 2058. PCI/PCIe devices can also be coupled to SB/ICH 2080 through a PCI bus 2062.

The PCI devices may include, for example, Ethernet adapters, add-in cards, and PC cards for notebook computers. The Hard disk drive 2060 and CD-ROM666 can use, for example, an integrated drive electronics (IDE) or serial advanced technology attachment (SATA) interface. In one implementation the I/O bus can include a super I/O (SIO) device.

Further, the hard disk drive (HDD) 2060 and optical drive 2066 can also be coupled to the SB/ICH 2020 through a system bus. In one implementation, a keyboard 2070, a mouse 2072, a parallel port 2078, and a serial port 2076 can be connected to the system bus through the I/O bus. Other peripherals and devices that can be connected to the SB/ICH 2020 using a mass storage controller such as SATA or PATA, an Ethernet port, an ISA bus, a LPC bridge, SMBus, a DMA controller, and an Audio Codec.

Moreover, the present disclosure is not limited to the specific circuit elements described herein, nor is the present disclosure limited to the specific sizing and classification of these elements. For example, the skilled artisan will appreciate that the circuitry described herein may be adapted based on changes on battery sizing and chemistry or based on the requirements of the intended back-up load to be powered.

Figure 22:
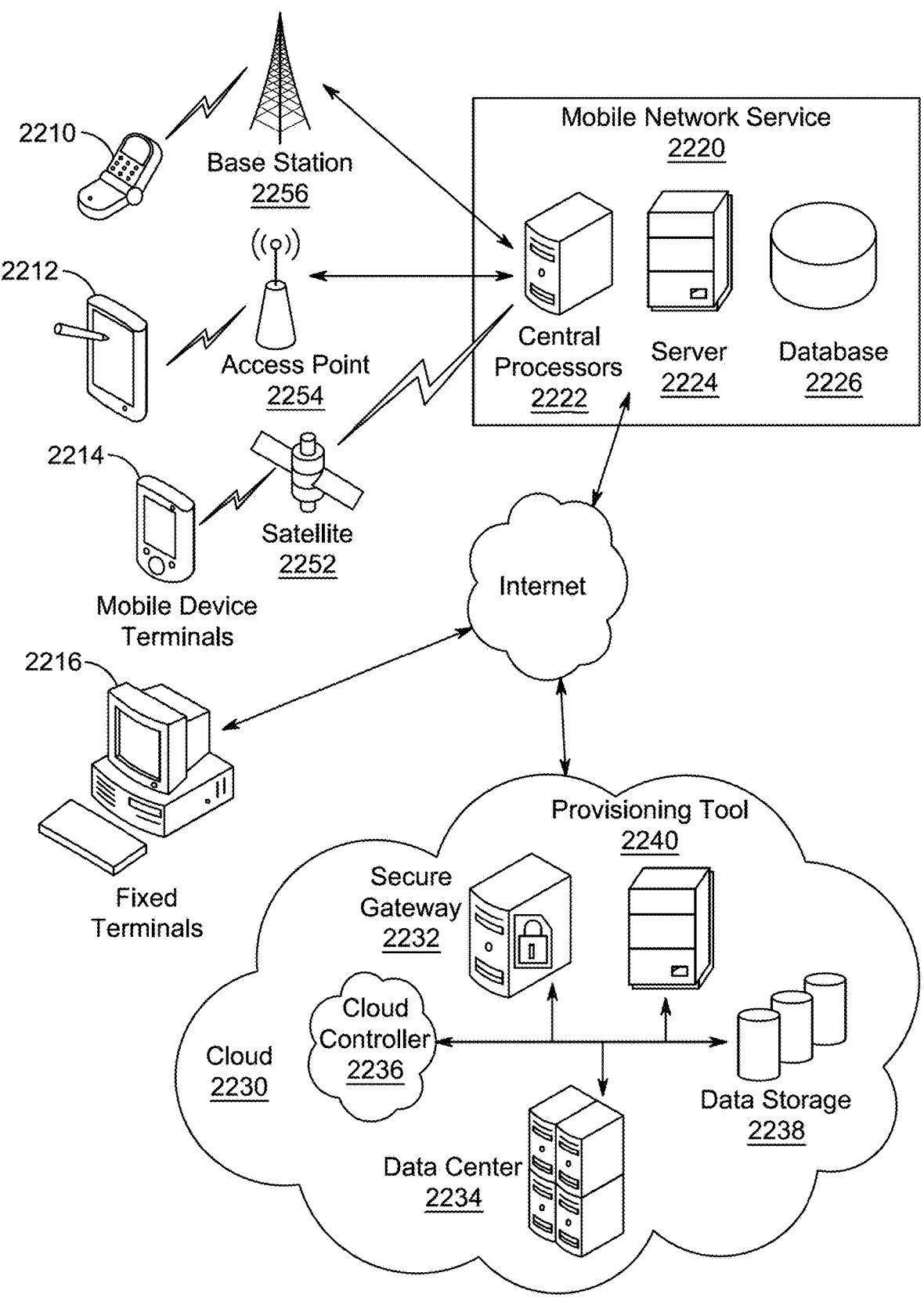
FIG. 22 is an illustration of a non-limiting example of distributed components which may share processing with a controller, according to certain embodiments.

The functions and features described herein may also be executed by various distributed components of a system. For example, one or more processors may execute these system functions, wherein the processors are distributed across multiple components communicating in a network. The distributed components may include one or more client and server machines, which may share processing, as shown by FIG. 22, in addition to various human interface and communication devices (e.g., display monitors, smart phones, tablets, personal digital assistants (PDAs)). The network may be a private network, such as a LAN or WAN, or may be a public network, such as the Internet. Input to the system may be received via direct user input and received remotely, either in real-time or as a batch process. Additionally, some aspects of the present disclosures may be performed on modules or hardware not identical to those described. Accordingly, other aspects of the present disclosures are within the scope that may be claimed. More specifically, FIG. 10 illustrates client devices including smart phone 2211, tablet 2212, mobile device terminal 2214 and fixed terminals 2216. These client devices may be commutatively coupled with a mobile network service 2220 via base station 2256, access point 2254, satellite 2252 or via an internet connection. Mobile network service 2220 may comprise central processors 2222, server 2224 and database 2226. Fixed terminals 2216 and mobile network service 2220 may be commutatively coupled via an internet connection to functions in cloud 2230 that may comprise security gateway 2232, data center 2234, cloud controller 2236, data storage 2238 and provisioning tool 2240.

The above-described hardware description is a non-limiting example of corresponding structure for performing the functionality described herein.

Numerous modifications and variations of the present disclosure are possible in light of the above teachings. It is therefore to be understood that within the scope of the appended claims, the invention may be practiced otherwise than as specifically described herein.

The invention claimed is:

1. A method for generating a multimodal diagnostic output related to a pathological condition of a patient, comprising:

receiving, by at least one processor, medical image data and narrative data of the patient;

preprocessing, by the at least one processor, the medical image data and the narrative data by normalizing the medical image data and standardizing the narrative data;

providing the preprocessed medical image data as inputs to a trained deep residual network (ResNet) to extract one or more quantitative imaging features indicative of the pathological condition;

providing the preprocessed narrative data as inputs to a thematic analysis module for extracting one or more thematic codes representing emotional, cognitive or social factors of the patient from the narrative data;

fusing vector representations of the one or more quantitative imaging features and the one or more thematic codes into a combined feature vector; and providing the combined feature vector as inputs into an integrated diagnostic model configured to generate the multimodal diagnostic output related to the pathological condition of the patient;

wherein the thematic analysis module comprises an automated coding engine that assigns preliminary thematic codes to segments using a hybrid approach that combines rule-based pattern matching with supervised or unsupervised machine learning; and wherein the thematic analysis module further includes a coder adjudication interface that allows human coders to review and reconcile codes when automated confidence falls below a configured threshold.

2. The method of claim 1, wherein receiving the medical image data and the narrative data comprises:

receiving the medical image data comprising a plurality of histopathological images and a plurality of radiological images related to the pathological condition including cancer; and receiving the narrative data comprising a text-based qualitative input from the patient through one or more of patient interviews, surveys and other textual information related to patient experiences and perceptions.

3. The method of claim 1, wherein preprocessing the medical image data further comprises image resizing and image augmentation, including at least one of rotation, scaling or flipping.

4. The method of claim 1, wherein standardizing the narrative data comprises tokenizing the narrative data, removing stop-words, and lemmatizing the narrative data.

5. The method of claim 1, wherein the trained deep residual network comprises a ResNet-50 architecture including a plurality of residual connections configured to learn one or more residual functions by applying a sequence of operations including convolution, batch normalization, and activation.

6. The method of claim 1, wherein inputting the preprocessed narrative data into the thematic analysis module for extracting one or more thematic codes further comprises performing, by the thematic analysis module, thematic coding, comprising:

labelling one or more narrative segments of the narrative data with the one or more thematic codes;

grouping the one or more thematic codes into one or more emotional, cognitive, or social factors of the patient;

generating one or more structured outputs that quantify the one or more emotional, cognitive, or social factors; and vectorizing the one or more structured outputs for the fusing.

7. The method of claim 1, wherein fusing the vector representations of the one or more quantitative imaging features and the one or more thematic codes comprises:

concatenating the vector representations of the one or more quantitative imaging features and the one or more thematic codes in a feature fusion layer;

applying adaptive weighting of the one or more quantitative imaging features and the one or more thematic codes;

aligning the one or more quantitative imaging features and the one or more thematic codes using a common patient identifier; and fusing the vector representations of the one or more quantitative imaging features and the one or more thematic codes through a shared neural layer.

8. The method of claim 1, wherein the multimodal diagnostic output comprises at least one of:

a diagnostic classification including a presence, a subtype or a stage of the pathological condition;

a confidence score; and a qualitative risk summary including a narrative-driven interpretation indicating at least one of emotional profile, cognitive profile or social factors of the patient.

9. The method of claim 1, wherein the trained deep residual network is pre-trained on a generic image dataset and fine-tuned on medical imaging data to extract the one or more quantitative imaging features.

10. The method of claim 1, further comprising receiving a clinical diagnostic outcome of the patient and updating at least one of the trained deep residual network or the thematic analysis module based on the clinical diagnostic outcome.

11. The method of claim 1, further comprising training and validating the integrated diagnostic model in a simulation environment by:

generating a plurality of synthetic histopathological images using a generative adversarial network trained on a plurality of domain-specific medical images, generating synthetic narrative data using a natural language generation model trained on domain-specific patient narratives; and evaluating performance of the integrated diagnostic model, comprising a meta-classifier or an ensemble program configured to process the combined feature vector, using at least one performance metric selected from accuracy, precision, recall, F1 score, thematic coherence, and thematic relevance.

12. A system for generating a multimodal diagnostic output related to a pathological condition of a patient, comprising:

at least one processor; and a memory storing instructions that, when executed by the at least one processor, cause the at least one processor to:

receive medical image data and narrative data of the patient;

preprocess the medical image data and the narrative data by normalization of the medical image data and standardization of the narrative data;

input the preprocessed medical image data into a trained deep residual network (ResNet) to extract one or more quantitative imaging features indicative of the pathological condition;

input the preprocessed narrative data into a thematic analysis module to extract one or more thematic codes representing emotional, cognitive or social factors of the patient from the narrative data;

fuse vector representations of the one or more quantitative imaging features and the one or more thematic codes into a combined feature vector; and input the combined feature vector into an integrated diagnostic model configured to generate the multimodal diagnostic output related to the pathological condition of the patient;

wherein the thematic analysis module comprises an automated coding engine that assigns preliminary thematic codes to segments using a hybrid approach that combines rule-based pattern matching with supervised or unsupervised machine learning; and wherein the thematic analysis module further includes a coder adjudication interface that allows human coders to review and reconcile codes when automated confidence falls below a configured threshold.

13. The system of claim 12, wherein the medical image data comprises a plurality of histopathological images and a plurality of radiological images related to the pathological condition, including cancer, and wherein the narrative data comprises a text-based qualitative input obtained from the patient through patient interviews, surveys or other textual information related to patient experiences and perceptions.

14. The system of claim 12, wherein the at least one processor is configured to:

preprocess the medical image data by image resizing and image augmentation that includes at least one of rotation, scaling, and flipping, and standardize the narrative data by tokenizing the narrative data, removing stop-words, and lemmatizing the narrative data.

15. The system of claim 12, wherein the at least one processor is configured to:

label one or more narrative segments of the narrative data with the one or more thematic codes;

group the one or more thematic codes into one or more emotional, cognitive or social factors of the patient;

generate one or more structured outputs that quantify the one or more emotional, cognitive or social factors; and vectorize the one or more structured outputs for the fusion.

16. The system of claim 12, wherein the trained deep residual network comprises a ResNet-50 architecture including a plurality of residual connections configured to learn one or more residual functions by applying a sequence of operations including convolution, batch normalization and activation.

17. The system of claim 12, wherein the at least one processor is configured to perform fusion of the one or more quantitative imaging features and the one or more thematic code, the at least one processor is configured to:

concatenate the vector representations of the one or more quantitative imaging features and the one or more thematic codes in a feature fusion layer;

apply adaptive weighting of the one or more quantitative imaging features and the one or more thematic codes;

align the one or more quantitative imaging features and the one or more thematic codes using a common patient identifier; and fuse the respective vector representations of the one or more quantitative imaging features and the one or more thematic codes through a shared neural layer.

18. The system of claim 12, wherein the at least one processor is configured to:

utilize a generic image dataset to pre-train the deep residual network; and utilize medical imaging data to fine-tune the pre-trained deep residual network to extract the one or more quantitative imaging features.

19. The system of claim 12, wherein the at least one processor is configured to receive a clinical diagnostic outcome of the patient and update at least one of the trained deep residual network or the thematic analysis module based on the clinical diagnostic outcome.

20. The system of claim 12, wherein the at least one processor is further configured to train and validate the integrated diagnostic model in a simulation environment, the at least one processor is configured to:

generate a plurality of synthetic histopathological images using a generative adversarial network trained on a plurality of domain-specific medical images, and generate synthetic narrative data using a natural language generation model trained on domain-specific patient narratives; and evaluate performance of the integrated diagnostic model, comprising a meta-classifier or an ensemble program configured to process the combined feature vector, using at least one performance metric selected from accuracy, precision, recall, F1 score, thematic coherence and thematic relevance.

* * * * *